US012668584B2

(12) United States Patent
Hsieh et al.

(10) Patent No.: US 12,668,584 B2
(45) Date of Patent: Jun. 30, 2026

(54) HETEROCYCLIC COMPOUNDS AS KINASE INHIBITORS FOR THERAPEUTIC USES

(71) Applicant: National Health Research Institutes, Miaoli County (TW)

(72) Inventors: Hsing-Pang Hsieh, Miaoli County (TW); Kun-Hung Lee, New Taipei City (TW); Wen-Hsing Lin, Miaoli County (TW); Chuan Shih, Carmel, IN (US)

(73) Assignee: National Health Research Institutes, Miaoli County (TW)

( * ) Notice: Subject to any disclaimer, the term of this patent is extended or adjusted under 35 U.S.C. 154(b) by 1294 days.

(21) Appl. No.: 17/603,273

(22) PCT Filed: Apr. 9, 2020

(86) PCT No.: PCT/US2020/027453

§ 371 (c)(1),
(2) Date: Oct. 12, 2021

(87) PCT Pub. No.: WO2020/210481

PCT Pub. Date: Oct. 15, 2020

(65) Prior Publication Data

US 2022/0213064 A1 Jul. 7, 2022

Related U.S. Application Data

(60) Provisional application No. 62/833,364, filed on Apr. 12, 2019.

(51) Int. Cl.

| | |
|---|---|
| ***C07D 401/14*** | (2006.01) |
| ***C07D 239/88*** | (2006.01) |
| ***C07D 401/04*** | (2006.01) |
| ***C07D 401/12*** | (2006.01) |

(52) U.S. Cl.

CPC ......... *C07D 401/14* (2013.01); *C07D 239/88* (2013.01); *C07D 401/04* (2013.01); *C07D 401/12* (2013.01)

(58) Field of Classification Search

CPC .................................................... C07D 401/14

See application file for complete search history.

(56) References Cited

U.S. PATENT DOCUMENTS

| | | | | |
|---|---|---|---|---|
| 6,797,823 | B1 | 9/2004 | Kubo et al. | |
| 7,253,286 | B2 * | 8/2007 | Funahashi ............ | A61K 31/517 546/153 |
| 7,495,104 | B2 | 2/2009 | Miwa et al. | |
| 2010/0249182 | A1 | 9/2010 | Yoo et al. | |
| 2012/0053192 | A1 | 3/2012 | Zhang et al. | |
| 2014/0275080 | A1 | 9/2014 | Flynn et al. | |
| 2016/0326162 | A1 | 11/2016 | Lin et al. | |
| 2017/0267660 | A1 | 9/2017 | Lin et al. | |
| 2017/0355676 | A1 | 12/2017 | Ratty et al. | |
| 2017/0355678 | A1 | 12/2017 | Bannen et al. | |

FOREIGN PATENT DOCUMENTS

| | | | | |
|---|---|---|---|---|
| CN | 104177346 | A | 12/2014 | |
| JP | 2007-516273 | A | 6/2007 | |
| JP | 2009-534410 | A | 9/2009 | |
| JP | 2010-528009 | A | 8/2010 | |
| JP | 2012-511535 | A | 5/2012 | |
| JP | 2012-526054 | A | 10/2012 | |
| JP | 2018-513150 | A | 5/2018 | |
| WO | WO-2005/030140 | A2 | 4/2005 | |
| WO | WO-2006117570 | A1 * | 11/2006 | ............. A61P 35/00 |
| WO | 2017/161045 | A1 | 9/2017 | |
| WO | WO-2018/071348 | A1 | 4/2018 | |
| WO | WO-2018/081276 | A1 | 5/2018 | |

OTHER PUBLICATIONS

Cannarile et al "Colony-Stimulating Factor 1 Receptor (CSF1R) Inhibitors in Cancer Therapy" Journal for Immuno Therapy of Cancer vol. 5, pp. 1-13, 2017.
Richters, et al., Targeting Gain of Function and Resistance Mutations in Alb and KIT by Hybrid Compound Design, Journal of Medicinal Chemistry, 56, 5757-5772, 2013.
International Search Report for International Application No. PCT/US20/27453 mailed Aug. 27, 2020.
Pubchem CID 67379395, Create Date: Nov. 30, 2012.
Pubchem CID 2814130, Create Date: Jul. 19, 2005.

* cited by examiner

*Primary Examiner* — John S Kenyon
*Assistant Examiner* — Rehana Ismail
(74) *Attorney, Agent, or Firm* — Morse, Barnes-Brown & Pendleton, P.C.; Lisa M. Warren, Esq.; Russell L. Widom

(57) ABSTRACT

Heterocyclic compounds of formula I shown below and pharmaceutical compositions containing one of such compounds: Also disclosed is a method of treating a condition modulated by the colony-stimulating factor-1 receptor with one of the heterocyclic compounds.

I

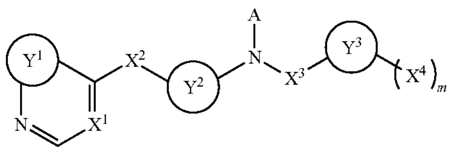

20 Claims, No Drawings

HETEROCYCLIC COMPOUNDS AS KINASE INHIBITORS FOR THERAPEUTIC USES

CROSS REFERENCE TO RELATED APPLICATIONS

This patent application is the national stage of International Patent Application No. PCT/US2020/027453, filed on Apr. 9, 2020, which claims the benefit and priority of U.S. Provisional Patent Application No. 62/833,364, filed on Apr. 12, 2019, the disclosures being incorporated by reference herein in their entirety as part of the present application.

BACKGROUND

Colony-stimulating factor-1 receptor (CSF1R) is a member of tyrosine kinase class III. It plays an important role in cell proliferation, differentiation, migration, and survival. See Cannarile et al., *J. Immunother. Cancer,* 2017, 5:53. Deregulation of this tyrosine kinase is associated with various disorders and diseases, such as inflammatory disorders, neurological disorders, cardiovascular diseases, bone-related diseases, and cancers.

Recent studies have shown that CSF1R is related to differentiation of tumor-associated macrophages (TAMs). See El-Gamal et al., *J. Med. Chem.,* 2018, 61, 5450-5466. Specifically, TAMs express, on their surfaces, CSF1R, which forms a signaling axis with an active ligand, i.e., colony stimulating factor-1 (CSF1). When activated, the CSF1R/CSF1 signaling axis promotes proliferation of monocytes, differentiation of the monocytes into TAMs, and survival of the TAMs.

Overexpression of CSF1 in several forms of cancer has been associated with activation and recruitment of TAMs to tumor sites. TAMs modify tumor microenvironment to render it more conducive to cancer cell growth, angiogenesis, and metastasis. Further, they can cause localized immunosuppression in tumor tissues, resulting in resistance to cancer therapy. As such, inhibiting the CSF1R/CSF1 signaling axis presents an attractive avenue for treating cancers associated with overexpression of CSF1.

Thus, there is a need to provide compounds that selectively inhibit CSF1R, demonstrate favorable safety profiles, and also exhibit high in vivo efficacy in treating cancers associated with CSF1R.

SUMMARY

The present invention is based on unexpected discoveries that certain heterocyclic compounds effectively inhibit colony-stimulating factor-1 receptor (CSF1R).

In one aspect, this invention relates to these heterocyclic compounds and other heterocyclic compounds analogous thereto covered by formula I:

I

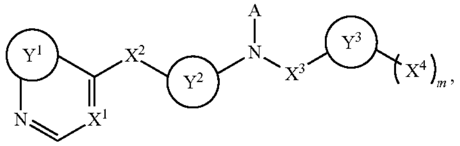

in which A is H, $C_{1-6}$ alkyl, or ORr, Rr being H or $C_{1-6}$ alkyl; $Y^1$ is phenyl substituted with $(R^1)_n$, 5-membered heteroaryl substituted with $(R^2)_o$, 5-membered heterocycloalkenyl substituted with $(R^2)_o$, or alkenyl substituted with $(R^2)_o$, in which $R^1$ in $(R^1)_n$, n being 0-4, is, independently, F, Cl, Br, $NO_2$, CN, amino, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_5$-$C_{15}$ heterocycloalkyl, aryl, heteroaryl, carbonyl, thionyl, iminyl, or spiroamino; and $R^2$ in $(R^2)_o$, o being 0-5, is, independently, F, Cl, Br, $NO_2$, CN, amino, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_5$-$C_{15}$ heterocycloalkyl, aryl, heteroaryl, carbonyl, thionyl, iminyl, spiroamino, or $C_1$-$C_6$ alkoxyl; $X^1$ is N or $CR^3$, $R^3$ being H, F, Cl, Br, CN, $C_1$-$C_6$ alkyl, $C_1$-$C_6$ haloalkyl, or $C_1$-$C_6$ alkoxyl; $X^2$ is O, S, NH, or $CH_2$; $Y^2$ is

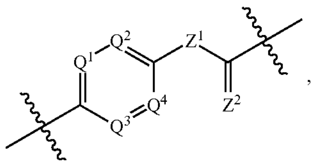,

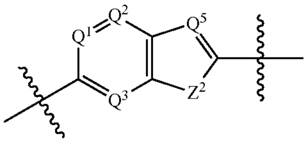,

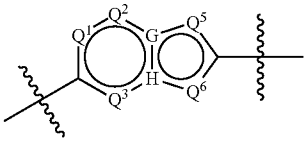,

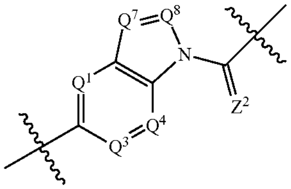, or

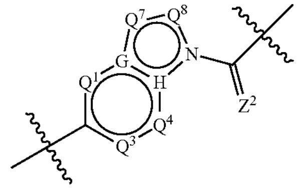, in which each of $Q^1$, $Q^2$, $Q^3$, $Q^4$, $Q^5$, $Q^6$, $Q^7$ and $Q^8$ is, independently, N or $CR^4$, $R^4$ being H, F, Cl, Br, CN, amino, $C_1$-$C_6$ alkyl, $C_1$-$C_6$ haloalkyl, or $C_1$-$C_6$ alkoxyl; $Z^1$ is O, S, or NRr; $Z^2$ is O, S, or NRr; and G and H are, respectively, C or N and N or C; $X^3$ is deleted, $CH_2$, $(CH_2)_2$, or $CH(C{\equiv}CH)$; $Y^3$ is $C_1$-$C_6$ alkyl, aryl, heteroaryl, $C_3$-$C_8$ cycloalkyl, or $C_5$-$C_6$ heterocycloalkyl having one heteroatom, in which the one heteroatom is O or N; and $X^4$ in $(X^4)_m$, m being 0-5, is, independently, F, Cl, Br, CN, $SO_2NH_2$, amino, $C_1$-$C_6$ alkyl, or $C_1$-$C_6$ alkoxyl.

The term "alkyl" refers to a straight or branched monovalent hydrocarbon moiety containing 1-20 carbon atoms, e.g., methyl, ethyl, n-propyl, i-propyl, n-butyl, i-butyl, and t-butyl. The term "haloalkyl" refers to an alkyl group substituted with one or more halogen atoms. The term "alkenyl" refers to a straight or branched monovalent or bivalent hydrocarbon containing 2-20 carbon atoms and one or more double bonds, e.g., ethenyl, propenyl, propenylene, allyl, and 1,4-butadienyl. The term "alkynyl" refers to a straight or branched monovalent or bivalent hydrocarbon containing 2-20 carbon atoms and one or more triple bonds, e.g., ethynyl, ethynylene, 1-propynyl, 1- and 2-butynyl, and 1-methyl-2-butynyl. The term “aryl” refers to a monovalent 6-carbon monocyclic, 10-carbon bicyclic, 14-carbon tricyclic aromatic ring system, e.g., phenyl, naphthyl, and anthracenyl. The term “heteroaryl” refers to a monovalent aromatic 5-8 membered monocyclic, 8-12 membered bicyclic, or 11-14 membered tricyclic ring system having one or more heteroatoms (such as O, N, S, or Se), e.g., imidazolyl, pyrazoyl, oxazolyl, isoxazolyl, thiazolyl, isothiazolyl, pyridyl, pyrazinyl, pyrimidyl, pyridazinyl, furyl, and thienyl. The term “cycloalkyl” refers to a monovalent or bivalent saturated hydrocarbon ring system having 3 to 30 carbon atoms (e.g., $C_3$-$C_{12}$), e.g., cyclopropyl, cyclobutyl, cyclopentyl, cyclopentenyl, cyclohexyl, 1,4-cyclohexylene, cycloheptyl, and cyclooctyl. The term “cycloalkenyl” refers to a monovalent or bivalent non-aromatic hydrocarbon ring system having 3 to 30 carbons (e.g., $C_3$-$C_{12}$) and one or more double bonds, e.g., cyclopentenyl, cyclohexenyl, and cycloheptenyl. The term “heterocycloalkyl” refers to a monovalent or bivalent nonaromatic 5-8 membered monocyclic, 8-12 membered bicyclic, or 11-14 membered tricyclic ring system having one or more heteroatoms (such as O, N, S, or Se), e.g., piperidinyl, piperazinyl, pyrrolidinyl, dioxanyl, morpholinyl, tetrahydrofuranyl, and tetrahydropyranyl. The term “heterocycloalkenyl” refers to a monovalent or bivalent nonaromatic 5-8 membered monocyclic, 8-12 membered bicyclic, or 11-14 membered tricyclic ring system having one or more heteroatoms (such as O, N, S, or Se) and one or more double bonds. The term “amino” refers to a —NRR' moiety, in which R and R' are, independently, H, alkyl, alkenyl, alkynyl, cycloalkyl, cycloalkenyl, heterocycloalkyl, heterocycloalkenyl, aryl, heteroaryl, aralkyl, or heteroaralkyl. The term “carbonyl” refers to a —C(O)R moiety, in which R is H, alkyl, alkenyl, alkynyl, cycloalkyl, cycloalkenyl, heterocycloalkyl, heterocycloalkenyl, alkoxyl, amino, aryl, or heteroaryl. The term “thionyl” refers to a —S(O)R moiety, in which R is H, alkyl, alkenyl, alkynyl, cycloalkyl, cycloalkenyl, heterocycloalkyl, heterocycloalkenyl, alkoxyl, amino, aryl, or heteroaryl. The term “iminyl” refers to a —C(NR)R', in which R is H or $C_1$-$C_6$ alkyl and R' is H, alkyl, alkenyl, alkynyl, cycloalkyl, cycloalkenyl, heterocycloalkyl, heterocycloalkenyl, alkoxyl, amino, aryl, or heteroaryl. The term “spiroamino” refers to a monovalent 7-11 membered bicyclic spiro moiety containing one N or a monovalent 10-16 membered tricyclic spiro moiety containing one N.

In addition, alkyl, alkenyl, alkynyl, aryl, heteroaryl, cycloalkyl, cycloalkenyl, heterocycloalkyl, heterocycloalkenyl, and alkoxyl can be substituted or unsubstituted. Possible substituents include, but are not limited to, D, CN, $NO_2$, halo, $C_1$-$C_{20}$ alkyl, $C_2$-$C_{20}$ alkenyl, $C_2$-$C_{20}$ alkynyl, $C_1$-$C_{10}$ alkoxyl, $C_3$-$C_{30}$ cycloalkyl, $C_3$-$C_{30}$ cycloalkenyl, $C_3$-$C_{30}$ heterocycloalkyl, $C_3$-$C_{30}$ heterocycloalkenyl, aryl, aryloxyl, heteroaryl, heteroaryloxyl, amino, halo, oxo (O═), thioxo (S═), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, acyl, thioacyl, acyloxy, carbamido, carbamyl, carboxyl, and carboxylic ester.

The compounds of formula I include the compounds themselves, as well as their salts, their stereoisomers, their solvates, their tautomers, their deuterated analogues, and their prodrugs, if applicable. A salt, for example, can be formed between an anion and a positively charged group (e.g., ammonium) on a heterocyclic compound of this invention. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a heterocyclic compound. Suitable cations include sodium ion, potassium ion, magnesium ion, calcium ion, and an ammonium cation such as tetramethylammonium ion. The salts of the heterocyclic compounds of this invention can also contain quaternary nitrogen atoms. Examples of prodrugs include esters and other pharmaceutically acceptable derivatives, which, upon administration to a subject, are capable of providing active heterocyclic compounds. A solvate refers to a complex formed between an active heterocyclic compound and a pharmaceutically acceptable solvent, e.g., water, ethanol, isopropanol, ethyl acetate, acetic acid, and ethanolamine.

An additional aspect of this invention relates to a pharmaceutical composition containing one or more of the heterocyclic compounds covered by formula I. The pharmaceutical composition can be used for treatment of a CSF1R modulated condition.

Also within the scope of this invention is a method of treating a CSF1R modulated condition, e.g., a cancer, an inflammatory disorder, a bone disorder, or an autoimmune disease. The method includes administering to a subject in need thereof an effective amount of one or more of the above-described heterocyclic compounds.

The term “treatment” or “treating” refers to administering one or more heterocyclic compounds of this invention to a subject who has a CSF1R modulated condition, a symptom of such a condition, or a predisposition toward it, with the purpose of conferring a therapeutic or prophylactic effect. “An effective amount” refers to the amount of an active compound that is required to confer such effect. Effective doses will vary, as recognized by those skilled in the art, depending on the types of disease treated, route of administration, excipient usage, and the possibility of co-usage with other therapeutic treatment.

A pharmaceutical composition of this invention can be administered parenterally, orally, nasally, rectally, topically, or buccally. The term “parenteral” as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer’s solution, and isotonic sodium chloride solution. In addition, fixed oils are conventionally employed as a solvent or suspending medium (e.g., synthetic mono- or di-glycerides). Fatty acids, such as oleic acid and its glyceride derivatives, are useful in preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A pharmaceutical composition of this invention can also be administered in the form of a suppository for rectal administration.

The carrier in a pharmaceutical composition must be "acceptable" in the sense that it is compatible with the active ingredient of the composition and, preferably, capable of stabilizing the active ingredient, and not deleterious to the subject to be treated. One or more solubilizing agents can be utilized as pharmaceutical excipients for delivery of an active heterocyclic compound of this invention. Examples of other carriers include colloidal silicon oxide, magnesium stearate, cellulose, sodium lauryl sulfate, and D&C Yellow #10.

The details of the invention are set forth in the description below. Other features, objects, and advantages of the invention will be apparent from the following detailed description of several embodiments, and also from the appending claims.

DETAILED DESCRIPTION

Disclosed first in detail are heterocyclic compounds of formula I:

I

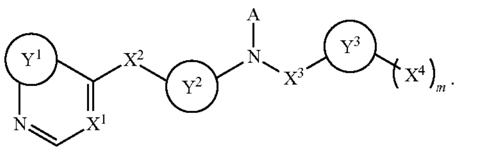

A, $Y^1$, $X^1$, $X^2$, $Y^2$, $X^3$, $Y^3$, $X^4$, and m are defined in the SUMMARY section above.

In one embodiment, the compounds of formula I have $Y^1$ being phenyl substituted with $(R^1)_n$, 5-membered heteroaryl substituted with $(R^2)_o$, or 5-membered heterocycloalkenyl substituted with $(R^2)_o$, in which $R^1$ in $(R^1)_n$ is, independently, F, Cl, Br, $NO_2$, CN, $C_1$-$C_6$ alkyl, $C_1$-$C_6$ haloalkyl, $C_2$-$C_6$ alkynyl, $C_3$-$C_8$ cycloalkyl, $C_5$-$C_{15}$ heterocycloalkyl, aryl, heteroaryl, carbonyl, thionyl, iminyl, or spiroamino; and $R^2$ in $(R^2)_o$ is, independently, F, Cl, Br, $NO_2$, CN, amino, $C_1$-$C_6$ alkyl, $C_1$-$C_6$ haloalkyl, $C_2$-$C_6$ alkynyl, $C_3$-$C_8$ cycloalkyl, $C_5$-$C_{15}$ heterocycloalkyl, aryl, heteroaryl, carbonyl, thionyl, iminyl, spiroamino, or $C_1$-$C_6$ alkoxyl.

In one subset of this embodiment, the compounds of formula I have $Y^2$ being

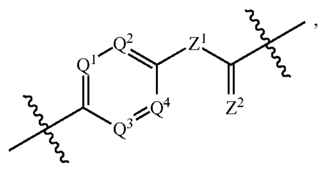

$Y^3$ being pyridyl, and $R^1$ being $C_5$-$C_{15}$ heterocycloalkyl.

In another embodiment, the compounds of formula I have $Y^2$ being

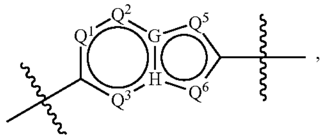

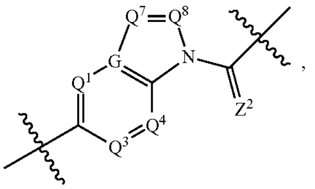

, or

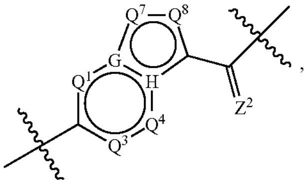

in which $Z^2$ is O or NRr.

In one subset of this embodiment, the compounds of formula I have $Y^2$ being

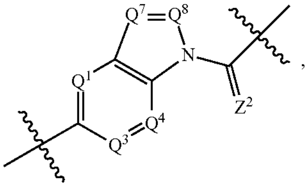

$Y^3$ being pyridyl, and $R^1$ being amino.

In still another embodiment, the compounds of formula I are those covered by formula Ia:

Ia

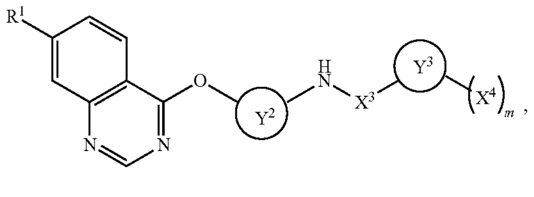

in which $R^1$ is amino or $C_5$-$C_{15}$ heterocycloalkyl.

In one subset of this embodiment, the compounds of formula Ia have $Y^2$ being

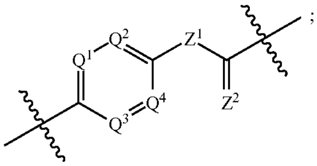

$Y^3$ being pyridyl; $X^3$ being $CH_2$; $X^4$ being $CH_3$, $CH_2F$, $CHF_2$, $CF_3$, or $OCH_3$, m being 1; and $R^1$ preferably being amino.

In another subset, the compounds have $Y^2$ being

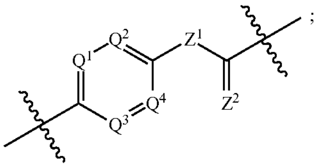

$Y^3$ being phenyl; $X^3$ being $CH_2$; each of $X^4$ being, independently, F, Cl, Br, CN, $SO_2NH_2$, $CH_3$, $CH_2F$, $CHF_2$, $CF_3$, $OCF_3$, $C_1$-$C_6$ alkoxyl, or amino; and m being 0-2.

In a third subset, the compounds have $Y^2$ being

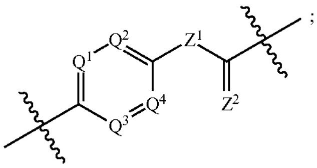

$Y^3$ being phenyl; $X^3$ being deleted; each of $X^4$ being, independently, F, Cl, Br, CN, $SO_2NH_2$, $CH_3$, $CH_2F$, $CHF_2$, $CF_3$, $OCF_3$, $C_1$-$C_6$ alkoxyl, or amino; and m being 0-2.

Formula Ia includes compounds in which $Y^2$ is

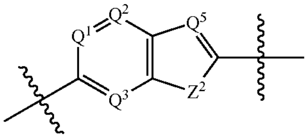

or

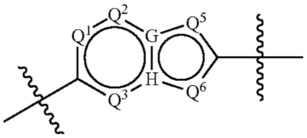

, $Y^3$ is phenyl or pyridyl, and $X^3$ is $CH_2$. As an example, $Y^2$ is

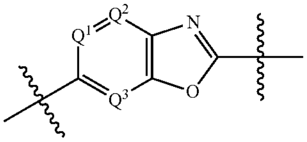

.

Formula Ia further includes compounds in which $Y^2$ is

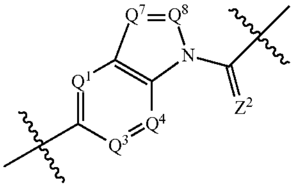

or

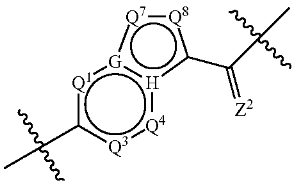

, $Y^3$ is phenyl or pyridyl, and $X^3$ is $CH_2$. For instance, $Y^2$ is

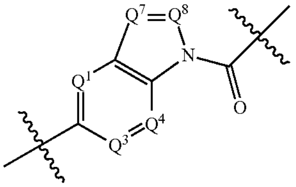

.

In a fourth embodiment, the heterocyclic compounds of this invention are covered by formula Ib:

Ib

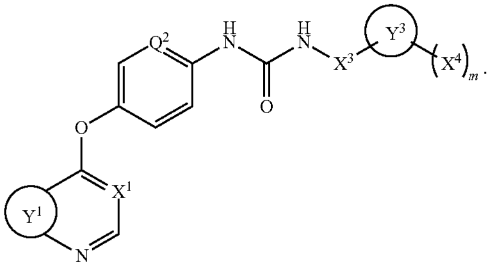

A subset of compounds of formula Ib have $Y^1$ being

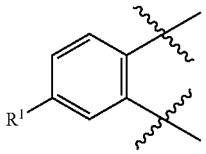

, $Y^3$ being phenyl or pyridyl; and $X^3$ being deleted or $CH_2$.

In a different subset, compounds of formula Ib have $Y^1$ being

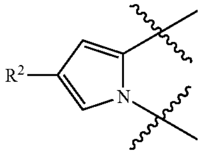

,

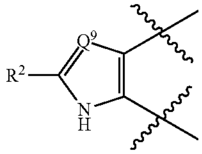

, or

-continued

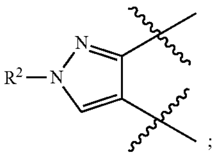

$Y^3$ being phenyl or pyridyl; and $X^3$ being deleted or $CH_2$, in which $Q^9$ is N or $CR^5$, $R^5$ being H, F, Cl, Br, CN, amino, $C_1$-$C_6$ alkyl, $C_1$-$C_6$ haloalkyl, or $C_1$-$C_6$ alkoxyl.

In another subset, compounds of this formula have $Y^1$ being

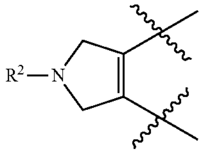

or

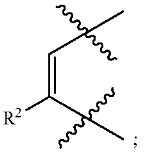

;

$Y^3$ being phenyl or pyridyl; and $X^3$ being deleted or $CH_2$.

Typically, the compounds of formula Ib have each of $X^4$ being, independently, $CH_3$, $CH_2F$, $CHF_2$, $CF_3$, or $OCH_3$ and m being 0-2.

Exemplary compounds of formula I include, but are not limited to, the following compounds:

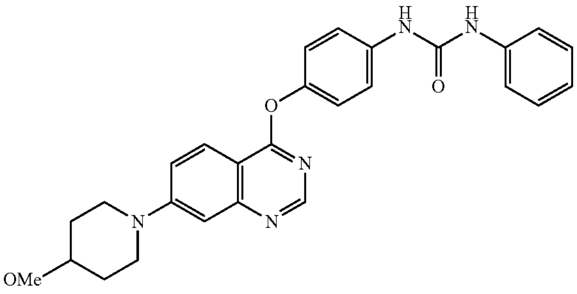

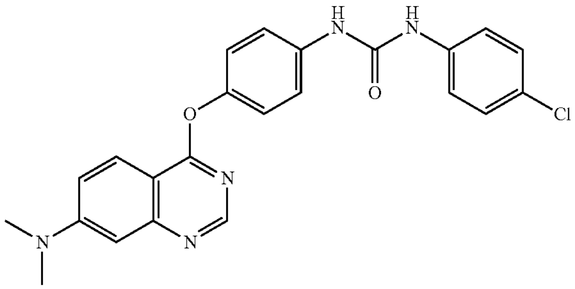

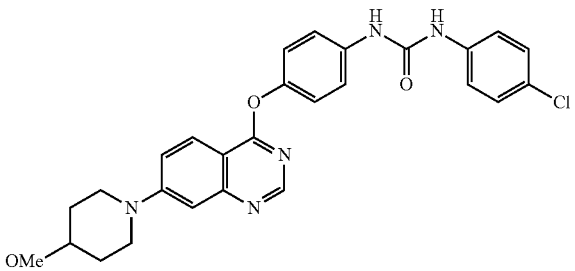

-continued

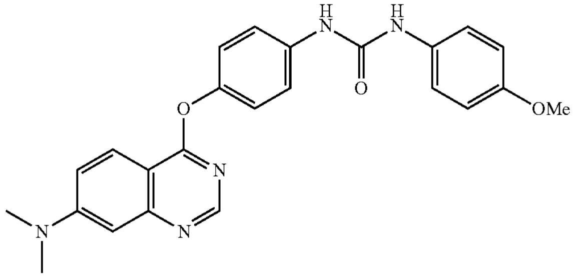

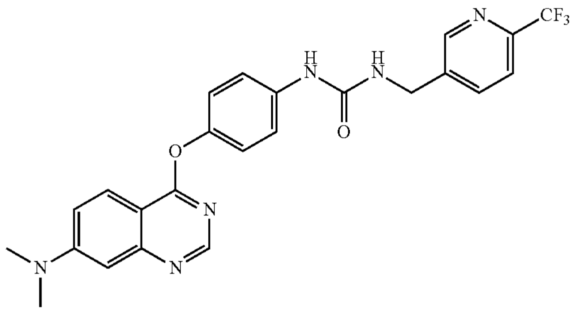

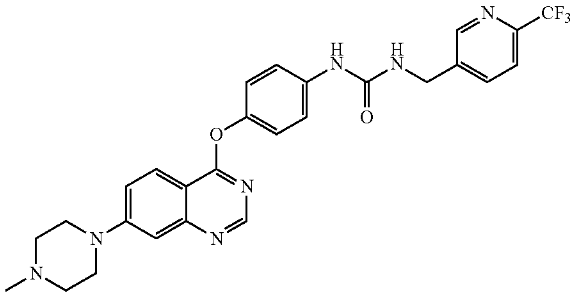

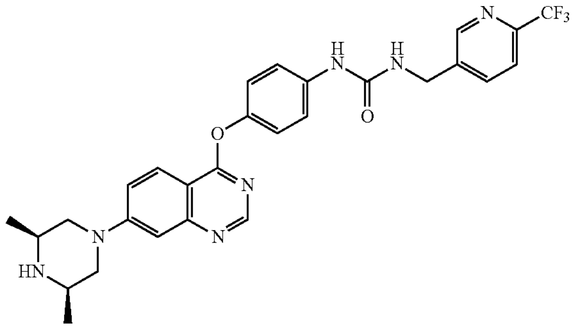

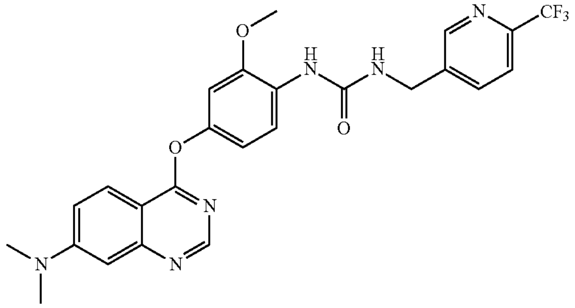

-continued
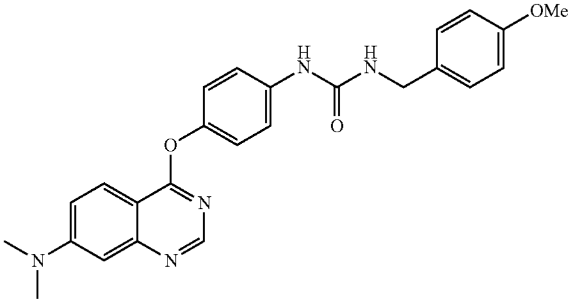
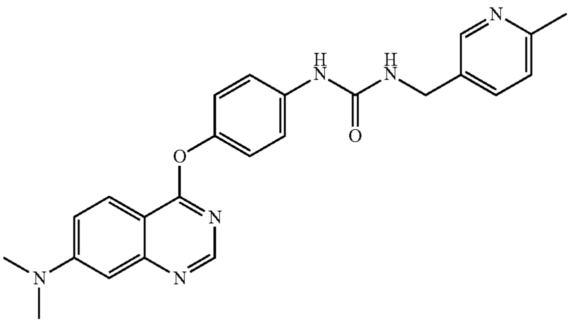
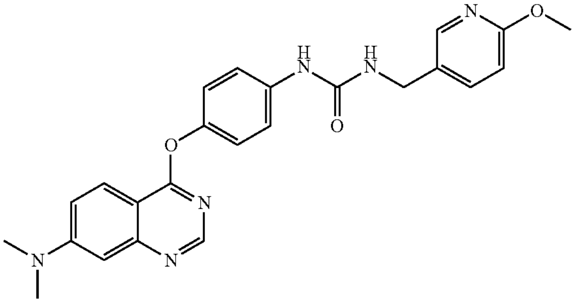
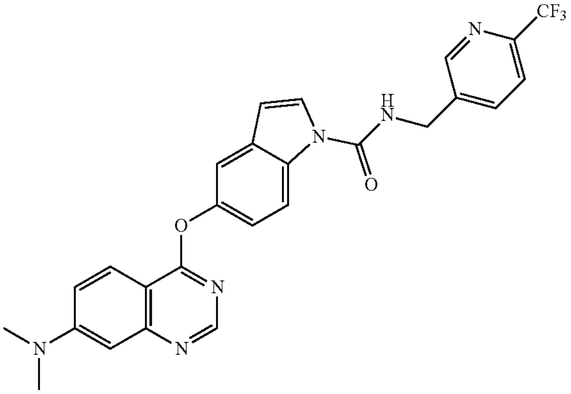
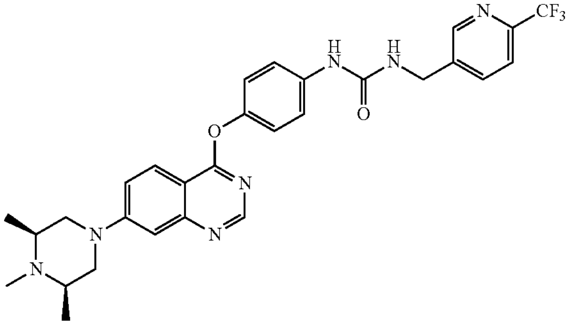
-continued
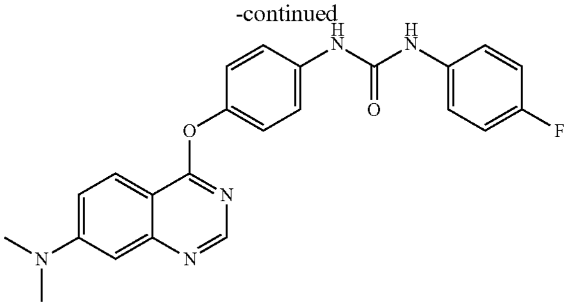
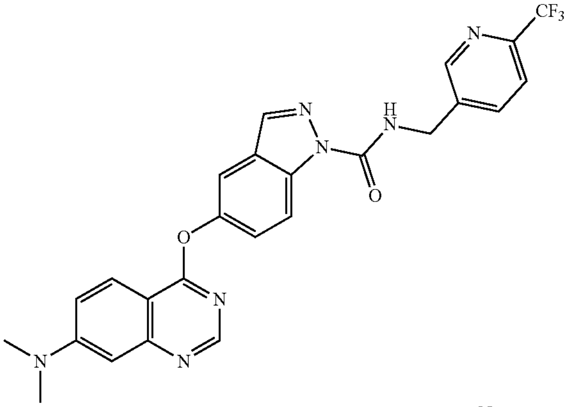
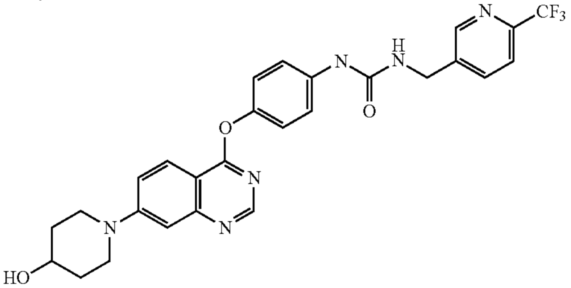
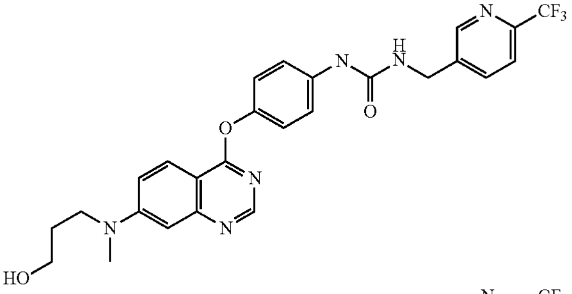
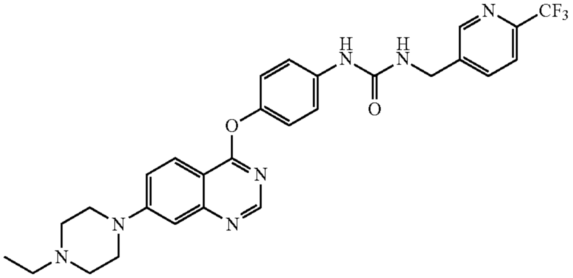
The compounds of formula I can be prepared according to methods well known in the field. See, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2nd ed., John Wiley and Sons 2009); and G. J. Yu et al., *J. Med. Chem.* 2008, 51, 6044-6054.

Also within the scope of this invention is a pharmaceutical composition containing one or more of the heterocyclic compounds of formula I. The pharmaceutical composition is used for treating a CSF1R modulated condition.

In certain embodiments, the pharmaceutical composition further contains one of the following therapeutic agents: an anti-proliferative agent, an anti-inflammatory agent, an immunomodulatory agent, and an immunosuppressive agent.

In other embodiments, the pharmaceutical composition further contains one of the following therapeutic agents: an alkylating agent, e.g., adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibody, e.g., alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; a targeted signal transduction inhibitor, e.g., bortezomib, geldanamycin, and rapamycin; a kinase inhibitor, e.g., erlotinib, gefitinib, flavopiridol, imatinib mesylate, lapatinib, sorafenib, sunitinib malate, AEE-788, AG-013736, AMG 706, AMN107, BMS-354825, BMS-599626, 7-hydroxystaurosporine, vemurafenib, dabrafenib, trametinib, cobimetinib, selumetinib, and vatalanib; a taxane, e.g., DJ-927, docetaxel, TPI 287, paclitaxel, and DHA-paclitaxel; a retinoid, e.g., alitretinoin, bexarotene, fenretinide, isotretinoin, and tretinoin; an alkaloid, e.g., etoposide, homoharringtonine, teniposide, vinblastine, vincristine, vindesine, and vinorelbine; an antibiotic, e.g., bleomycin, dactinomycin, daunorubicin, doxorubicin, epirubicin, idarubicin, menogaril, mitomycin, mitoxantrone, neocarzinostatin, pentostatin, and plicamycin; an antiangiogenic agent, e.g., AE-941, ABT-510, 2-methoxyestradiol, lenalidomide, and thalidomide; a topoisomerase inhibitor, e.g., amsacrine, edotecarin, exatecan, irinotecan, 7-ethyl-10-hydroxy-camptothecin, rubitecan, topotecan, and 9-aminocamptothecin; an antimetabolite, e.g., azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; a hormone or hormone antagonist, e.g., anastrozole, androgens, buserelin, diethylstilbestrol, exemestane, flutamide, fulvestrant, goserelin, idoxifene, letrozole, leuprolide, magestrol, raloxifene, tamoxifen, and toremifene; a biological response modifier, e.g., imiquimod, interferon-α, and interleukin-2; an indoleamine 2,3-dioxygenase inhibitor; a chemotherapeutic agent, e.g., 3-amino-2-carboxy aldehyde thiosemicarbazone, altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, and tiazofurin; a mammalian target of rapamycin inhibitor; a phosphoinositide 3-kinase inhibitor; a cyclin-dependent kinase 4 inhibitor; a protein kinase B inhibitor; a heat shock protein 90 inhibitor; a farnesyltransferase inhibitor; an aromatase inhibitor (such as anastrozole, letrozole, and exemestane); a mitogen-activated protein kinase kinase inhibitor; a tyrosine kinase inhibitor; an epidermal growth factor receptor inhibitor; a programmed cell death protein 1 inhibitor; a programmed death-ligand 1 inhibitor; or an interleukin 8 receptor beta inhibitor.

Still within the scope of this invention is a method of treating a CSF1R modulated condition using one or more of the above-described heterocyclic compounds. For example, the condition can be a cancer, e.g., acute myeloid leukemia, bladder cancer, breast cancer, cervical cancer, colon cancer, gastric cancer, gastrointestinal stromal tumor, glioblastoma multiforme, hepatocellular carcinoma, Hodgkin's lymphoma, kidney cancer, liver cancer, lung cancer, melanoma, metastatic tumor, ovarian cancer, pancreatic cancer, pigmented villondular synovitis, prostate cancer, tenosynovial giant cell tumors, endometrial cancer, multiple myeloma, myelocytic leukemia, bone cancer, renal cancer, brain cancer, myeloproliferative disorder, esophageal cancer, squamous cell carcinoma, uveal melanoma, follicular lymphoma, colorectal cancer, head and neck cancer, astrocytoma, and pulmonary adenocarcinoma; an inflammatory disorder or an autoimmune disease, e.g., psoriatic arthritis, arthritis, asthma, thyroiditis, glomerular nephritis, atherosclerosis, psoriasis, Sjogren's syndrome, rheumatoid arthritis, systemic lupus erythematosis, cutaneous lupus erythematosus, Crohn's disease, ulcerative colitis, type I diabetes, multiple sclerosis, human immunodeficiency virus encephalitis, Alzheimer's disease, amyotrophic lateral sclerosis, and epilepsy; or a bone disorder, e.g., osteoporosis, osteoarthritis, periodontitis, periprosthetic osteolysis, and Paget's disease.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

Example 1: Synthesis of Heterocyclic Compounds

Exemplary compounds of this invention, shown in Table 1 below, were prepared by procedures shown in Scheme 1, Scheme 2, Scheme 3, or Scheme 4. Table 1 includes mass spectral data for the compounds.

All chemicals and solvents were purchased from commercial suppliers and used as received. All reactions were carried out under an atmosphere of dry nitrogen unless specified otherwise. Reactions were monitored by thin layer chromatography using Merck 60 F254 silica gel glass backed plates (5×10 cm) and zones were detected visually under ultraviolet irradiation (254 nm) or by spraying with phosphomolybdic acid reagent (Aldrich) followed by heating at 80° C. Microwave reactions were performed in the CEM Discover SP System.

Flash column chromatography was performed by using Merck Kieselgel 60, No. 9385, 230-400 mesh ASTM silica gel as the stationary phase. Proton nuclear magnetic resonance ($^1$H NMR) spectra were measured on a Varian Mercury-300 or Varian Mercury-400 spectrometer. Chemical shifts were recorded in parts per million (ppm) on the delta (6) scale relative to the resonance of the solvent peak. The following abbreviations were used to describe coupling: s=singlet; d=doublet; t=triplet; q=quartet; quin=quintet; ABq=AB quartet; AA'XX'=second order AA'XX' pattern; app.=apparent; br=broad; and m=multiplet.

Liquid chromatography mass spectrometry (LCMS) data was obtained with an Agilent MSD-1100 ESI-MS/MS, an Agilent 1200 series LC/MSD VL, or a Waters Acquity UPLC-ESI-MS/MS system.

Scheme 1

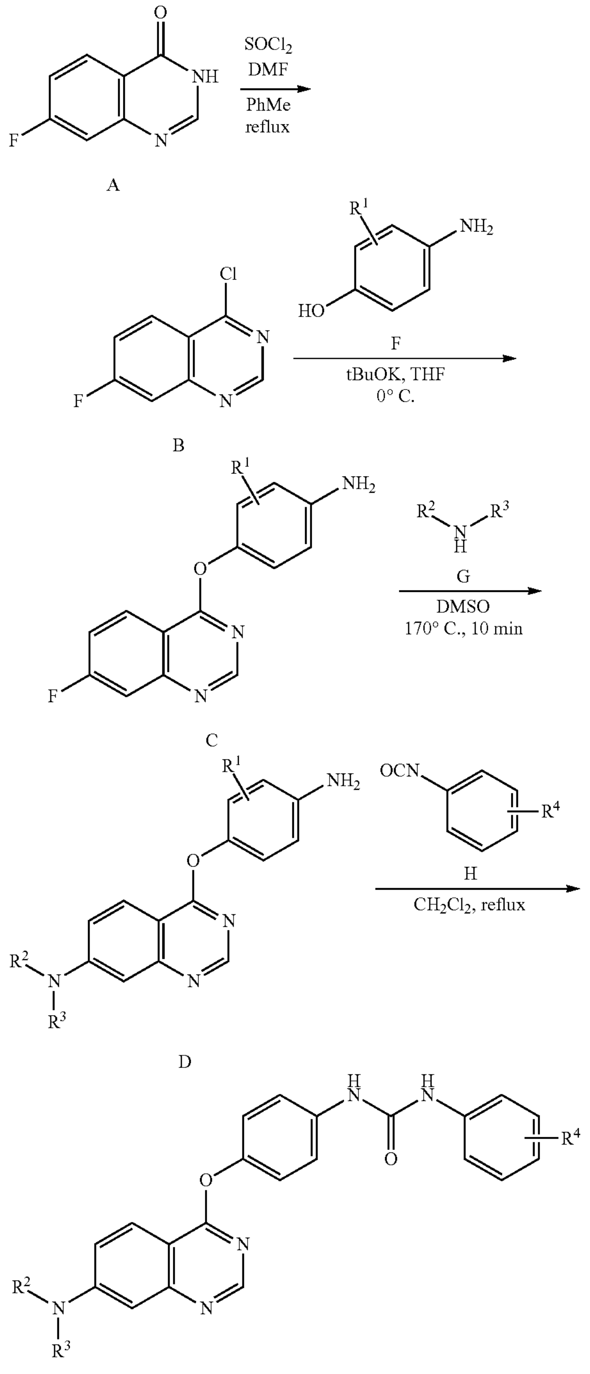

Among the listed reagents and solvents in Scheme 1, $SOCl_2$ is thionylchloride, DMF is dimethylformamide, PhMe is toluene, tBuOK is potassium tert-butoxide, THF is tetrahydrofuran, DMSO is dimethylsulfoxide, and $CH_2Cl_2$ is methylene chloride.

4-Chloro-7-fluoroquinazoline (B). To a suspension of 7-fluoroquinazolin-4-ol compound A (6.32 g, 38.5 mmol) in dry PhMe (30 mL), $SOCl_2$ (22 mL, 7.7 eq.) and DMF (2.6 mL) were added. The resulting mixture was refluxed for 10 h. The mixture was then cooled to room temperature, quenched with water (200 mL), and extracted with ethyl acetate (EtOAc; 170 mL). The combined organic extracts were washed with water (300 mL) and brine (30 mL), dried over sodium sulfate ($NA_2SO_4$), and concentrated to afford compound B (6.08 g, 86%) as a yellow solid. LCMS (ESI) m/z calculated for $C_8H_4ClFN_2$: 182, 184; found: 183, 185 $[M+H]^+$. $^1$H-NMR (400 MHz, $CDCl_3$) δ 9.04 (s, 1H), 8.33 (dd, J=9.2 Hz, $^4J_{F,H}$=6.0 Hz, 1H), 7.71 (dd, $^3J_{F,H}$=9.2 Hz, J=2.4 Hz, 1H), 7.52 (ddd, J=9.2, 2.4 Hz, $^3J_{F,H}$=8.4 Hz, 1H).

4-((7-fluoroquinazolin-4-yl)oxy)aniline (C). A mixture of 4-aminophenol F (3.05 g, 28.0 mmol) and t-BuOK (3.14 g, 28.0 mmol) in dry THF (100 mL) was stirred for 20 min at 0° C. Subsequently, compound B (4.44 g, 24.3 mmol) was added slowly in small portions. The reaction mixture was then stirred for 3 h at 0° C., during which a suspension was formed. Afterwards, the suspension was filtered through a pad of celite, The pad was rinsed with THF. THF in the filtrate was removed by evaporation to give a crude residue. The residue was suspended in methanol (MeOH) and sonicated to form a solid. The solid was collected via filtration and dried to afford the titled product C (5.47 g, 88%) as an off-white solid. LCMS (ESI) m/z calculated for $C_{14}H_{10}BrN_3O$: 255; found: 256 $[M+H]^+$. $^1$H-NMR (400 MHz, $CDCl_3$) δ 8.76 (s, 1H), 8.40 (dd, J=9.2 Hz, $^4J_{F,H}$=6.0 Hz, 1H), 7.61 (dd, $^3J_{F,H}$=9.2 Hz, J=2.4 Hz, 1H), 7.40 (ddd, J=9.2, 2.4 Hz, $^3J_{F,H}$=8.8 Hz, 1H), 7.04 (AA'XX', $J_{AX}$=8.8 Hz, $J_{AX'}$=0 Hz, 2H), 6.77 (AA'XX', $J_{AX}$=8.8 Hz, $J_{AX'}$=0 Hz, 2H), 3.71 (br, 2H).

4-(4-aminophenoxy)-N,N-dimethylquinazolin-7-amine (D). To a solution of compound C (600 mg, 2.35 mmol) in DMSO (7.1 mL), 2 M dimethlyamine in THF (3 eq., 3.53 mL) was added. The mixture was then irradiated in microwave for 10 min at 170° C. After compound C was consumed, the reaction mixture was diluted with EtOAc (30 mL) and 2% sodium carbonate ($NA_2CO_3$) solution (80 mL), and extracted with EtOAc (50 mL). The combined organic extracts were sequentially washed with 2% $NA_2CO_3$ solution (160 mL), water (200 mL), and brine (20 mL), dried over $NA_2SO_4$, and concentrated. The crude residue was suspended in MeOH. Particles in the supension were collected via filtration and dried to afford the titled product D (207 mg, 32%) as a pale yellow solid. LCMS (ESI) m/z calculated for $C_{16}H_{16}N_4O$: 280; found: 281 $[M+H]^+$. $^1$H-NMR (300 MHz, $CDCl_3$): δ 8.58 (s, 1H), 8.15 (d, J=9.2 Hz, 1H), 7.12 (dd, J=9.2 Hz, J=2.7 Hz, 1H), 7.03 (AA'XX', $J_{AX}$=9.0 Hz, $J_{AX'}$=0 Hz, $J_{AA'}$=2.9 Hz, $J_{XX'}$=2.9 Hz, 2H), 6.96 (d, J=2.7 Hz, 1H), 6.75 (AA'XX', $J_{AX}$=9.0 Hz, $J_{AX'}$=0 Hz, $J_{AA'}$=2.9 Hz, $J_{XX'}$=2.9 Hz, 2H), 3.67 (br, 2H), 3.15 (s, 6H).

1-(4-((7-(dimethylamino)quinazolin-4-yl)oxy)phenyl)-3-phenylurea (compound 4, E). To a solution of compound D (165 mg, 0.588 mmol) in $CH_2Cl_2$ (15 mL), compound H (108 μL, 0.883 mmol) was added. The mixture was refluxed for 10 h, during which a suspension was formed. Particles in the suspension were collected via filtration and rinsed with excess $CH_2Cl_2$ to afford the titled product E (214 mg, 91%) as a white solid. LCMS (ESI) m/z calculated for $C_{23}H_{21}N_5O_2$: 399; found: 400 $[M+H]^+$. $^1$H-NMR (400 MHz, DMSO-$d_6$): δ 8.77 (br s, 1H), 8.71 (br s, 1H), 8.45 (s, 1H), 8.11 (d, J=9.6 Hz, 1H), 7.52 (AA'XX', $J_{AX}$=8.8 Hz, $J_{AX'}$=0 Hz, $J_{AA'}$=2.6 Hz, $J_{XX'}$=2.6 Hz, 2H), 7.47 (d, J=5.6 Hz, 2H), 7.32-7.27 (m, 3H), 7.19 (AA'XX', $J_{AX}$=8.8 Hz, $J_{AX'}$=0 Hz, $J_{AA'}$=2.6 Hz, $J_{XX'}$=2.6 Hz, 2H), 6.97 (t, J=7.2 Hz, 1H), 6.88 (d, J=2.4 Hz, 1H), 3.12 (s, 6H).

Compounds 1, 2, 3, 5, 6, 7, 9, 10, 11, 12, 13, 14, 15, 16, 17, 18, 19, 20, 21, 52, and 106 were prepared in a manner similar to compound 4, with appropriate amines G and isocyanates H.

Scheme 2

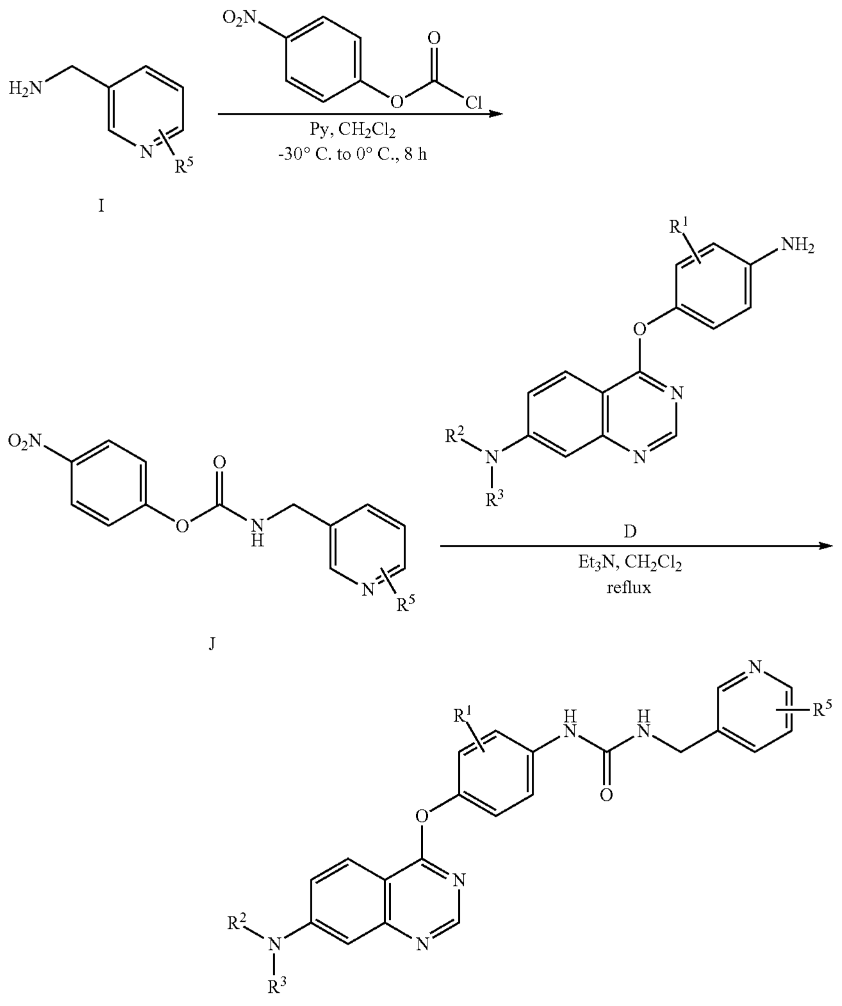

I

J

K

Among the listed reagents and solvents in Scheme 2, Py is pyridine, and $Et_3N$ is triethylamine.

4-nitrophenyl ((6-(trifluoromethyl)pyridin-3-yl)methyl) carbamate (J). To a −30° C. solution of (6-(trifluoromethyl) pyridin-3-yl)methanamine I (2.69 g, 15.3 mmol) and Py (1.23 mL, 15.3 mmol) in $CH_2Cl_2$ (50 mL), 4-nitrophenyl chloroformate (3.85 g, 19.1 mmol) was slowly added. The reaction mixture was stirred for 8 h and allowed to slowly warm to 0° C. Subsequently, water (50 mL) was added to the reaction mixture. The mixture was then stirred for 20 min, during which a suspension was formed. Particles in the suspension were removed by filtering the reaction mixture through a pad of celite. The filtrate was washed with 2% sodium bisulfate solution (20 mL), 2% sodium bicarbonate solution (40 mL), water (20 mL), and brine (3 mL), dried over $NA_2SO_4$, and concentrated. The crude residue was purified by column chromatography to afford the titled product J (3.33 g, quant.) as a white solid. LCMS (ESI) m/z calculated for $C_{14}H_{10}F_3N_3O_4$: 341; found: 342 $[M+H]^+$. $^1$H-NMR (400 MHz, $CDCl_3$): δ 8.73 (d, J=1.4 Hz, 1H), 8.26 (AA'XX', $J_{AX}$=9.2 Hz, $J_{AX'}$=0 Hz, $J_{AA'}$=2.6 Hz, $J_{XX'}$=2.6 Hz, 2H), 7.91 (dd, J=8.0, 1.4 Hz, 1H), 7.71 (d, J=8.0 Hz, 1H), 7.33 (AA'XX', $J_{AX}$=9.2 Hz, $J_{AX'}$=0 Hz, $J_{AA'}$=2.6 Hz, $J_{XX'}$=2.6 Hz, 2H), 5.68 (br t, 1H), 4.58 (d, J=6.4 Hz, 2H).

1-(4-((7-(dimethylamino)quinazolin-4-yl)oxy)phenyl)-3-((6-(trifluoromethyl)pyridin-3-yl)methyl)urea (compound 27, K). To a solution of compound J (2.19 g, 6.43 mmol) and compound D (1.06 g, 3.78 mmol) in $CH_2Cl_2$ (95 mL), $Et_3N$ (1.05 mL) was added. The reaction mixture was refluxed for 4 d, during which a suspension was formed. Particles in the suspension were collected via filtration and rinsed with excess $CH_2Cl_2$ to afford the titled product K (1.33 g, 73%) as a white solid. LCMS (ESI) m/z calculated for $C_{24}H_{21}F_3N_6O_2$: 482; found: 483 $[M+H]^+$. $^1$H NMR (400 MHz, DMSO-$d_6$): δ 8.83 (s, 1H), 8.72 (d, J=1.2 Hz, 1H), 8.43 (s, 1H), 8.10 (d, J=9.2 Hz, 1H), 8.00 (dd, J=8.4, 1.2 Hz, 1H), 7.89 (d, J=8.4 Hz, 1H), 7.47 (AA'XX', $J_{AX}$=8.8 Hz, $J_{AX'}$=0 Hz, $J_{AA'}$=2.6 Hz, $J_{XX'}$=2.6 Hz, 2H), 7.29 (d, J=9.2, 2.4 Hz, 1H), 7.13 (AA'XX', $J_{AX}$=8.8 Hz, $J_{AX'}$=0 Hz, $J_{AA'}$=2.6 Hz, $J_{XX'}$=2.6 Hz, 2H), 6.87 (d, J=2.4 Hz, 1H), 6.84 (t, J=6.0 Hz, 1H), 4.44 (d, J=6.0 Hz, 2H), 3.12 (s, 6H).

1-(4-((7-(dimethylamino)quinazolin-4-yl)oxy)phenyl)-3-((6-methylpyridin-3-yl)methyl)urea (compound 65, K) LCMS (ESI) m/z calculated for $C_{24}H_{21}F_3N_6O_2$: 428; found: 429 $[M+H]^+$. $^1$H NMR (400 MHz, DMSO-$d_6$) δ 8.68 (s, 1H), 8.43 (s, 1H), 8.39 (d, J=2.4 Hz, 1H), 8.10 (d, J=9.2 Hz, 1H), 7.61 (dd, J=8.0, 2.4 Hz, 1H), 7.46 (AA'XX', $J_{AX}$=8.8 Hz, 2H), 7.29 (dd, J=9.2, 2.4 Hz, 1H), 7.22 (d, J=8.0 Hz, 1H), 7.13 (AA'XX', $J_{AX}$=8.8 Hz, 2H), 6.87 (d, J=2.4 Hz, 1H), 6.67 (t, J=6.0 Hz, 1H), 4.28 (d, J=6.0 Hz, 1H), 3.12 (s, 6H), 2.44 (s, 3H).

1-(4-((7-(dimethylamino)quinazolin-4-yl)oxy)phenyl)-3-((6-methylpyridin-3-yl)methyl)urea (compound 66, K) LCMS (ESI) m/z calculated for $C_{24}H_{21}F_3N_6O_2$: 444; found: 445 $[M+H]^+$. $^1H$ NMR (400 MHz, DMSO-$d_6$) δ 8.68 (s, 1H), 8.43 (s, 1H), 8.39 (d, J=2.4 Hz, 1H), 8.10 (d, J=9.2 Hz, 1H), 7.61 (dd, J=8.0, 2.4 Hz, 1H), 7.46 (AA'XX', $J_{AX}$=8.8 Hz, 2H), 7.29 (dd, J=9.2, 2.4 Hz, 1H), 7.22 (d, J=8.0 Hz, 1H), 7.13 (AA'XX', $J_{AX}$=8.8 Hz, 2H), 6.87 (d, J=2.4 Hz, 1H), 6.67 (t, J=6.0 Hz, 1H), 4.28 (d, J=6.0 Hz, 1H), 3.12 (s, 6H), 2.44 (s, 3H).

Compounds 23, 24, 25, 28, 30, 33, 36, 39, 40, 42, 43, 44, 49, 50, 51, 54, 55, 56, 57, 58, 59, 60, 63, 65, 66, 87, 90, 91, 92, 96, and 101 were prepared in a manner similar to compound 27 with appropriate amines H and anilines D Scheme 3

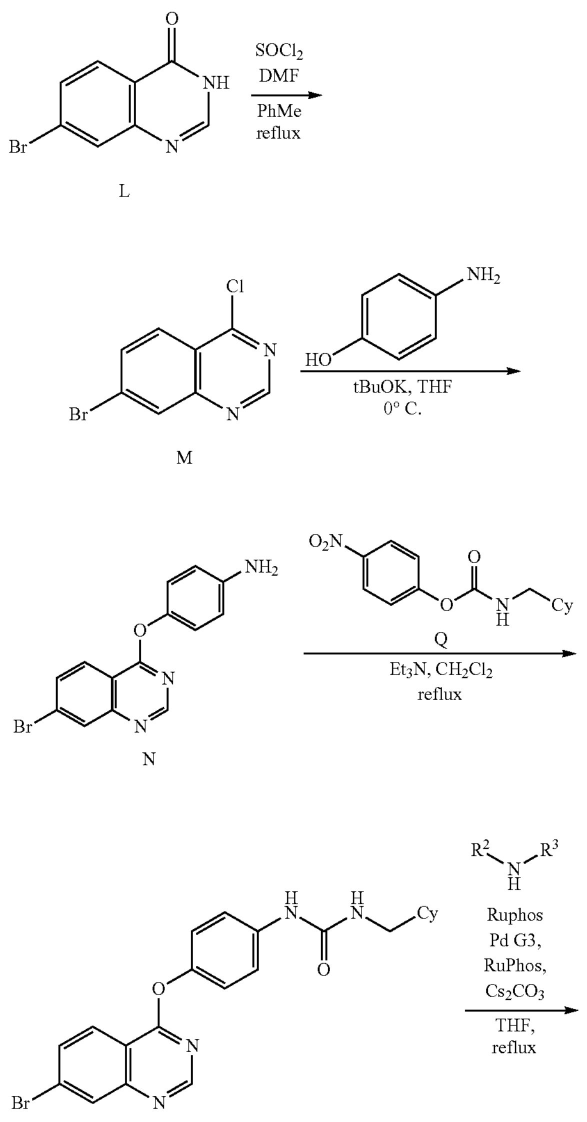

O

-continued

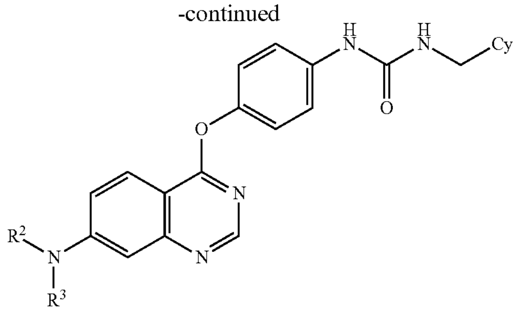

P

Among the listed reagents, solvents and catalysts in Scheme 3, $SOCl_2$ is thionylchloride, RuPhos Pd G3 is (2-dicyclohexylphosphino-2',6'-diisopropoxy-1,1'-biphenyl) [2-2'-amino-1,1'-biphenyl]] palladium(II) methanesulfonate, RuPhos is 2-dicyclohexylphosphino-2',6'-diisopropoxybiphenyl, and $Cs_2CO_3$ is cesium carbonate.

4-Chloro-7-bromoquinazoline (M). To a suspension of 7-bromoquinazolin-4-ol L (1.17 g, 5.20 mmol) in dry PhMe (6 mL), $SOCl_2$ (6 mL) and DMF (0.6 mL) were added. The resulting mixture was stirred at 95° C. for 9 h, cooled to room temperature, quenched with water (100 mL), and extracted with EtOAc (70 mL). The combined organic extracts were washed with water (200 mL) and brine (5 mL), dried over $NA_2SO_4$, and concentrated to afford the titled product M (1.26 g, 99%) as a yellow solid. LCMS (ESI) m/z calculated for $C_8H_4BrClN_2$: 242, 244, 246; found: 243, 245, 247 $[M+H]^+$. $^1H$-NMR (300 MHz, $CDCl_3$): δ 9.05 (s, 1H), 8.28 (d, J=1.8 Hz, 1H), 8.15 (d, J=9.0 Hz, 1H), 7.84 (dd, J=9.0, 1.8 Hz, 1H).

4-((7-Bromoquinazolin-4-yl)oxy)aniline (N). A mixture of 4-aminophenol (0.678 g, 6.21 mmol) and t-BuOK (0.668 g, 5.95 mmol) in dry THF (15 mL) at 0° C. was stirred for 20 min. Subsequently, 4-chloro-7-bromoquinazoline M (1.26 g, 5.17 mmol) was added slowly in small portions. The reaction mixture was then stirred for 3 h at 0° C., during which a suspension was formed. The suspension was filtered through a pad of celite. The pad was rinsed with THF (20 mL), and the resulting filtrate was evaporated to give a crude solid. The crude solid was suspended in MeOH (6 mL) and sonicated. Particles in the suspension were collected via filtration and dried to afford the titled product N (1.461 g, 89%) as an off-white solid. LCMS (ESI) m/z calculated for $C_{14}H_{10}BrN_3O$: 315, 317; found: 316, 318 $[M+H]^+$.

1-(4-((7-Bromoquinazolin-4-yl)oxy)phenyl)-3-((6-(trifluoromethyl)pyridin-3-yl)methyl)urea (O; compound 31). To a solution of 4-((7-Bromoquinazolin-4-yl)oxy)aniline N (305 mg, 0.964 mmol) and compound Q (461 mg, 1.35 mmol) in $CH_2Cl_2$ (6 mL), $Et_3N$ (0.27 mL) was added. The resulting mixture was refluxed for 1.5 d, during which a suspension was formed. Particles in the suspension was collected via filtration and rinsed with excess $CH_2Cl_2$ to afford the titled product O (462 mg, 93%) as a white solid. LCMS (ESI) m/z calculated for $C_{22}H_{15}BrF_3N_5O_2$: 517, 519; found: 518, 520 $[M+H]^+$. $^1H$ NMR (400 MHz, DMSO-$d_6$): δ 8.87 (s, 1H), 8.74 (s, 1H), 8.72 (br s, 1H), 8.30 (d, J=8.8 Hz, 1H), 8.24 (d, J=2.0 Hz, 1H), 8.00 (dd, J=8.0, 1.6 Hz, 1H), 7.93 (dd, J=8.8, 2.0 Hz, 1H), 7.90 (d, J=8.0 Hz, 1H), 7.50 (AA'XX', $J_{AX}$=9.0 Hz, $J_{AX'}$=0 Hz, 2H), 7.21 (AA'XX', $J_{AX}$=9.0 Hz, $J_{AX'}$=0 Hz, 2H), 6.86 (t, J=6.0 Hz, 1H), 4.44 (d, J=6.0 Hz, 2H).

1-(4-((7-(3,5-Dimethylpiperazin-1-yl)quinazolin-4-yl) oxy)phenyl)-3-((6-(trifluoromethyl)pyridin-3-yl)methyl)

urea (P; compound 34). Freshly-distilled THF (4 mL) was purged with argon for 20 min, after which compound O (50 mg, 0.097 mmol), $Cs_2CO_3$ (47 mg, 0.15 mmol), cis-2,6-dimethylpiperazine (17 mg, 0.15 mmol), Ruphos (4.1 mg, 0.009 mmol), and Ruphos Pd G3 (4.1 mg, 0.005 mmol) were added to form a suspension. The resulting mixture was stirred under argon for 5 min. Subsequently, the reaction mixture was refluxed overnight. The resulting pale-yellow solution was filtered through a pad of celite and the filtrate was concentrated to give a residue. The residue was purified by column chromatography to afford the titled product P (49 mg, 92%) as a white solid. LCMS (ESI) m/z calculated for $C_{28}H_{28}F_3N_7O_2$: 551; found: 552 $[M+H]^+$. $^1H$ NMR (400 MHz, DMSO-$d_6$): δ 8.85 (s, 1H), 8.72 (d, J=1.6 Hz, 1H), 8.46 (s, 1H), 8.09 (d, J=9.2 Hz, 1H), 8.00 (dd, J=8.0, 1.6 Hz, 1H), 7.90 (d, J=8.0 Hz, 1H), 7.51 (dd, J=9.2, 2.4 Hz, 1H), 7.47 (AA'XX', $J_{AX}$=9.2 Hz, $J_{AX'}$=0 Hz, 2H), 7.17-7.13 (m, 3H), 6.85 (t, J=5.6 Hz, 1H), 4.44 (d, J=5.6 Hz, 2H), 3.91-3.88 (m, 2H), 2.87-2.82 (m, 2H), 2.39-2.33 (m, 2H), 1.06 (d, J=6.4 Hz, 6H).

1-(4-((7-(4-hydroxypiperidin-1-yl)quinazolin-4-yl)oxy)phenyl)-3-((6-(trifluoromethyl)pyridin-3-yl)methyl)urea (P; compound 30). Similar to compound 34, compound 30 was prepared from compound 31 and was obtained as a white solid. LCMS (ESI) m/z calculated for $C_{28}H_{28}F_3N_7O_2$: 538; found: 539 $[M+H]^+$. $^1H$ NMR (400 MHz, DMSO-$d_6$): δ 8.82 (br s, 1H), 8.72 (d, J=1.2 Hz, 1H), 8.45 (s, 1H), 8.08 (d, J=9.2 Hz, 1H), 8.00 (dd, J=8.0, 1.2 Hz, 1H), 7.89 (d, J=8.0 Hz, 1H), 7.51-7.45 (m, 3H), 7.15-7.11 (m, 3H), 6.84 (t, J=6.0 Hz, 1H), 4.76 (d, J=4.0 Hz, 2H), 4.44 (d, J=6.0 Hz, 2H), 3.87-3.81 (m, 2H), 3.77-3.72 (m, 1H), 3.21-3.14 (m, 1H), 1.87-1.83 (m, 2H), 1.51-1.43 (m, 2H).

Compounds 24, 96, 97, 98, 99, 100 were prepared analogously to compound 34.

Scheme 4

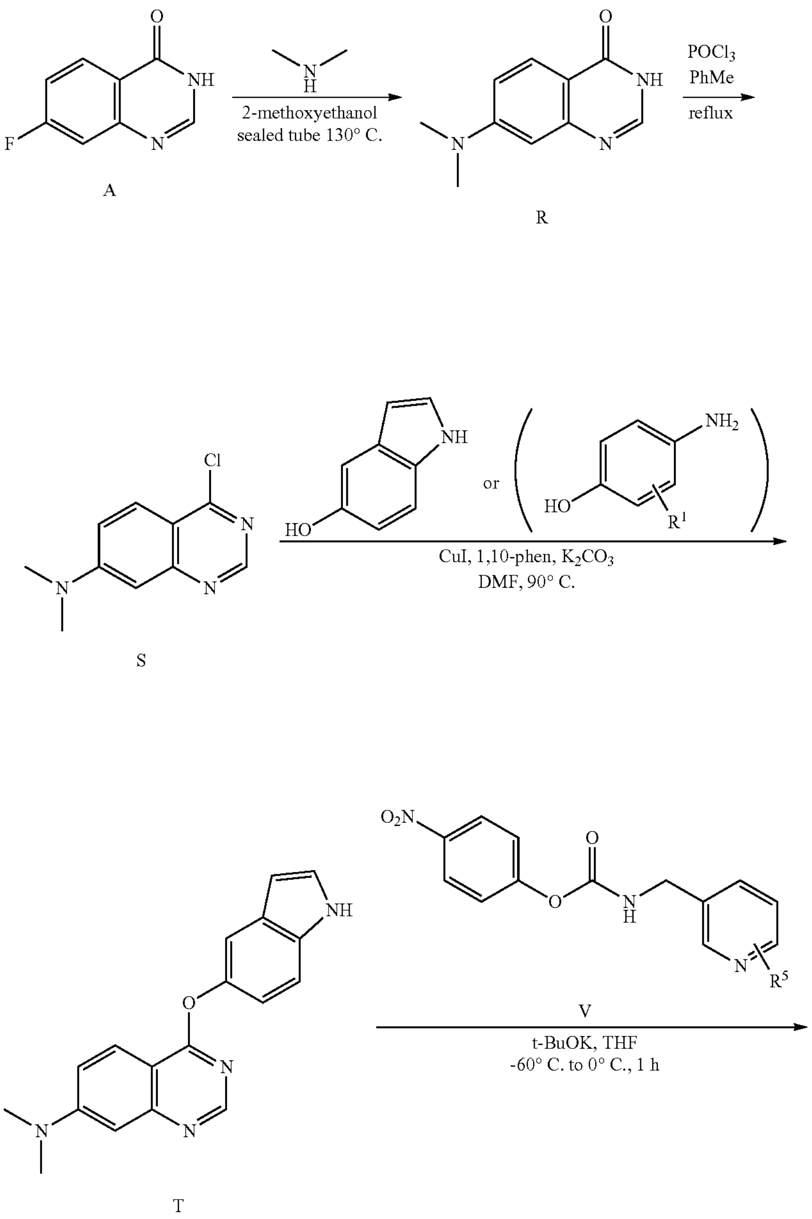

-continued

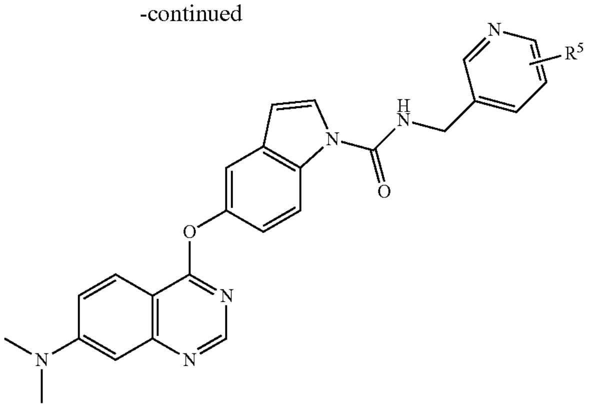

U

Among the listed reagents, solvents, and catalysts listed in Scheme 3, $POCl_3$ is phosphoryl chloride, CuI is copper iodide, 1,10-phen is 1,10-phenanthroline, $K_2CO_3$ is potassium carbonate, and tBuOH is tert-butanol.

7-(Dimethylamino)quinazolin-4(3H)-one (R). A solution of 7-fluoroquinazolin-4(3H)-one A (1.65 g, 10.1 mmol) and dimethylamine (2M in THF, 20 mL, 40.2 mmol) in 2-methoxyethanol (60 mL) in a 250 mL sealed tube was stirred at 130° C. for 1 d, during which a solid was formed. Subsequently, the reaction mixture was cooled to room temperature and concentrated under reduced pressure. The resulting residue was suspended in MeOH (8 mL) and filtered to afford the titled product R (1.5 g, 79%) as a brown solid. LCMS (ESI) m/z calculated for $C_{10}H_{11}N_3O$: 189; found: 190 $[M+H]^+$. $^1H$ NMR (300 MHz, DMSO-$d_6$): δ 11.69 (br, 1H), 7.91 (s, 1H), 7.88 (d, J=9.0 Hz, 1H), 6.93 (dd, J=9.0, 2.4 Hz, 1H), 6.98 (d, J=2.4 Hz, 1H), 3.04 (s, 6H).

4-Chloro-N,N-dimethylquinazolin-7-amine (S). To a suspension of 7-(dimethylamino)quinazolin-4(3H)-one R (910 mg, 4.81 mmol) in dry PhMe (10 mL), $POCl_3$ (4 mL) was added, after which the resulting mixture was stirred at 95° C. for 12 h. The reaction mixture was the cooled to 0° C., quenched with ice water (100 mL), and neutralized with saturated sodium carbonate solution until the color of the solution turned from bright orange to pale yellow. Subsequently, the reaction mixture was extracted with EtOAc (170 mL), and the organic extract was washed with water (200 mL) and brine (20 mL), dried over $NA_2SO_4$, and concentrated to afford the titled product S (948 mg, 95%) as a yellow solid. LCMS (ESI) m/z calculated for $C_{10}H_{10}ClN_3$: 207, 209; found: 208, 210 $[M+H]^+$. $^1H$-NMR (300 MHz, $CDCl_3$): δ 8.77 (s, 1H), 8.03 (d, J=9.3 Hz, 1H), 7.20 (dd, J=9.3, 2.7 Hz, 1H), 6.96 (d, J=2.7 Hz, 1H), 3.18 (s, 1H).

4-((1H-indol-5-yl)oxy)-N,N-dimethylquinazolin-7-amine (T). DMF (4 mL) was purged with argon. Subsequently, 4-Chloro-N,N-dimethylquinazolin-7-amine S (322 mg, 1.55 mmol), 5-hydroxyindole (413 mg, 3.10 mmol), $K_2CO_3$ (429 mg, 3.10 mmol), CuI (29.5 mg, 0.155 mmol), and 1,10-phen (27.9 mg, 0.155 mmol) were added to form a reaction mixture, which was stirred at 90° C. for 3 h under argon. The reaction mixture was then diluted with EtOAc (15 mL) and water (15 mL), and filtered through a pad of celite. The filtrate was extracted with EtOAc (60 mL), and the organic extract was washed with water (120 mL) and brine (5 mL), dried over $NA_2SO_4$, and concentrated. The residue was suspended in MeOH and particles were collected by filtration to afford the titled product T (381 mg, 81%) as a white solid. LCMS (ESI) m/z calculated for $C_{18}H_{16}N_4O$: 304; found: 305 $[M+H]^+$.

5-((7-(dimethylamino)quinazolin-4-yl)oxy)-N-((6-(trifluoromethyl)pyridin-3-yl)methyl)-1H-indole-1-carboxamide (U; compound 67). To a solution of 4-(4-amino-3-methoxyphenoxy)-N,N-dimethylquinazolin-7-amine T (170 mg, 0.95 mmol) in dry THF (5 mL), NaH (60% in oil, 112 mg, 2.79 mmol) was added. The resulting mixture was stirred at room temperature for 20 min. Subsequently, the mixture was cooled to −60° C., and 4-nitrophenyl ((6-(trifluoromethyl)pyridin-3-yl)methyl)carbamate V (574 mg, 1.68 mmol) was added in 3 portions. The mixture was then slowly warmed to 0° C., stirred for 1 h, and quenched with saturated ammonium chloride solution. The solvent was removed under reduced pressure and the resulting residue was diluted with EtOAc (35 mL), washed with water (80 mL) and brine (3 mL), dried over $NA_2SO_4$, and concentrated. The crude residue was purified by column chromatography to afford the titled product U (171 mg, 65%) as a white solid. LCMS (ESI) m/z calculated for $C_{26}H_{21}F_3N_6O_2$: 506; found: 507 $[M+H]^+$. $^1H$ NMR (400 MHz, DMSO-$d_6$): δ 8.94 (t, J=5.6 Hz, 1H), 8.82 (d, J=1.6 Hz, 1H), 8.41 (s, 1H), 8.27 (d, J=8.8 Hz, 1H), 8.15 (d, J=9.2 Hz, 1H), 8.10 (dd, J=8.0, 1.6 Hz, 1H), 7.96 (d, J=3.6 Hz, 1H), 7.92 (d, J=8.0 Hz, 1H), 7.50 (d, J=2.4 Hz, 1H), 7.31 (dd, J=9.2, 2.4 Hz, 1H) 7.16 (dd, J=8.8, 2.4 Hz, 1H), 6.88 (d, J=2.4 Hz, 1H), 6.74 (d, J=3.6 Hz, 1H), 4.64 (d, J=5.6 Hz, 2H), 3.13 (s, 6H).

Compounds 29, 35, 38, 64, 68, 69, 83, and 89 were prepared in a manner similar to compound 67.

TABLE 1
| Exemplary heterocyclic compounds | | | |
|---|---|---|---|
| Compound | Structure | Calculated Mass | Mass [M + H]$^+$ |
| 1 | 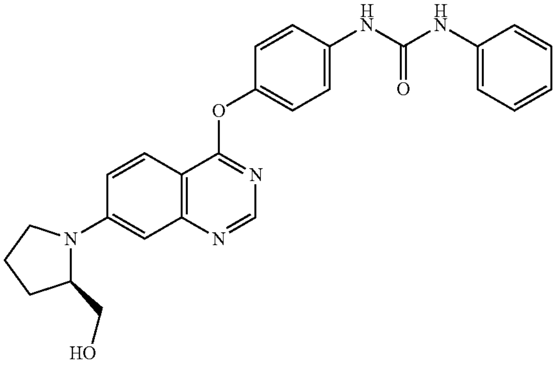 [SMILES: O=C(Nc1ccccc1)Nc1ccc(Oc2ncnc3cc(N4CCC[C@@H]4CO)ccc23)cc1] | 455 | 456 |
| 2 | 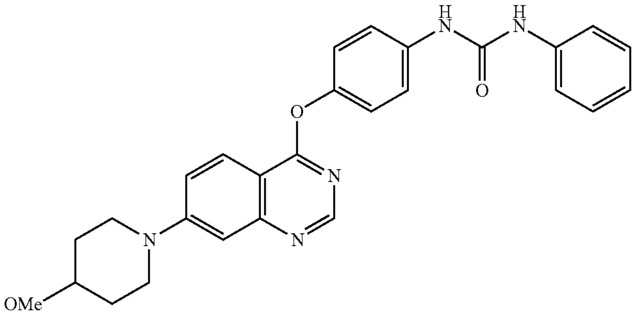 [SMILES: COC1CCN(c2ccc3c(Oc4ccc(NC(=O)Nc5ccccc5)cc4)ncnc3c2)CC1] | 469 | 470 |
| 3 | 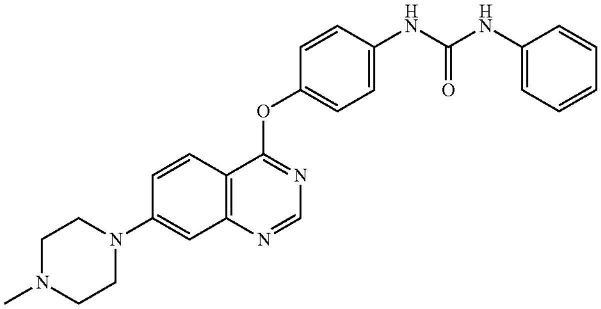 [SMILES: CN1CCN(c2ccc3c(Oc4ccc(NC(=O)Nc5ccccc5)cc4)ncnc3c2)CC1] | 454 | 455 |
| 4 | 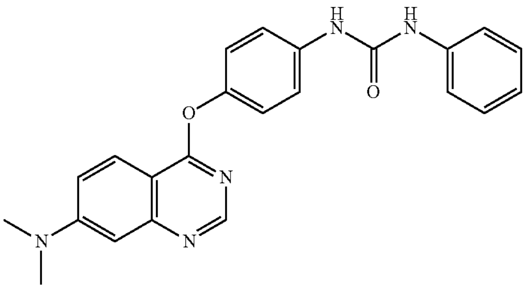 [SMILES: CN(C)c1ccc2c(Oc3ccc(NC(=O)Nc4ccccc4)cc3)ncnc2c1] | 399 | 400 |

TABLE 1-continued
| Exemplary heterocyclic compounds | | | |
|---|---|---|---|
| Compound | Structure | Calculated Mass | Mass $[M + H]^+$ |
| 5 | 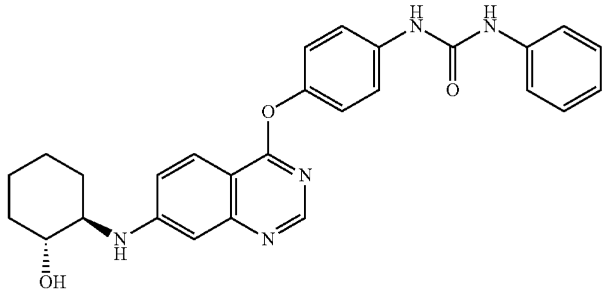 [SMILES: O=C(Nc1ccccc1)Nc1ccc(Oc2ncnc3cc(N[C@@H]4CCCC[C@H]4O)ccc23)cc1] | 469 | 470 |
| 6 | 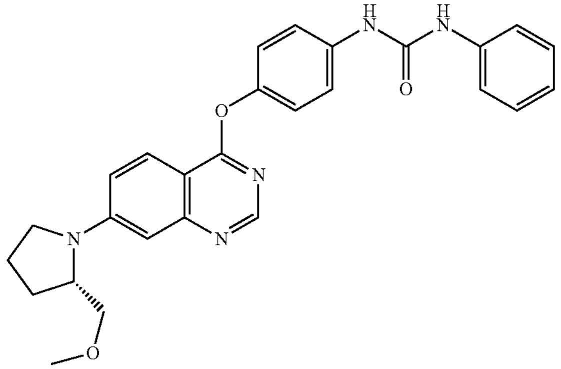 [SMILES: COC[C@@H]1CCCN1c1ccc2c(Oc3ccc(NC(=O)Nc4ccccc4)cc3)ncnc2c1] | 469 | 470 |
| 7 | 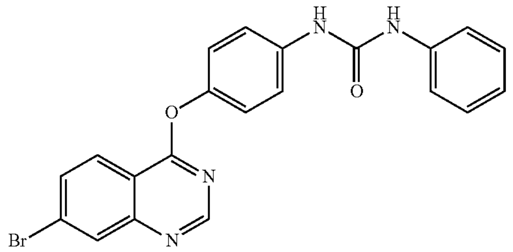 [SMILES: O=C(Nc1ccccc1)Nc1ccc(Oc2ncnc3cc(Br)ccc23)cc1] | 434 | 435 |
| 8 | 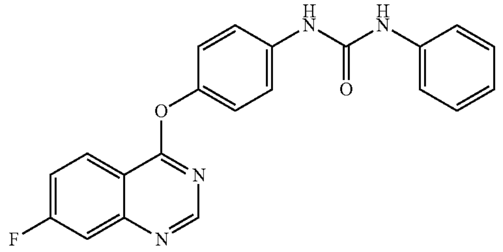 [SMILES: O=C(Nc1ccccc1)Nc1ccc(Oc2ncnc3cc(F)ccc23)cc1] | 374 | 375 |
| 9 | 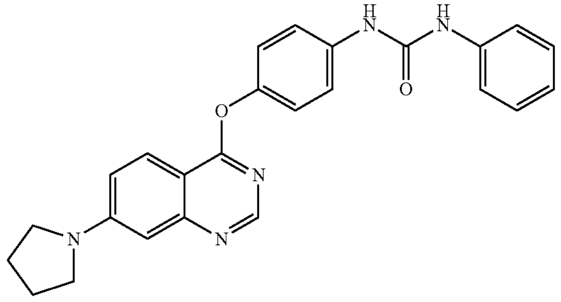 [SMILES: O=C(Nc1ccccc1)Nc1ccc(Oc2ncnc3cc(N4CCCC4)ccc23)cc1] | 425 | 426 |

TABLE 1-continued
| Exemplary heterocyclic compounds | | | |
|---|---|---|---|
| Compound | Structure | Calculated Mass | Mass [M + H]+ |
| 10 | 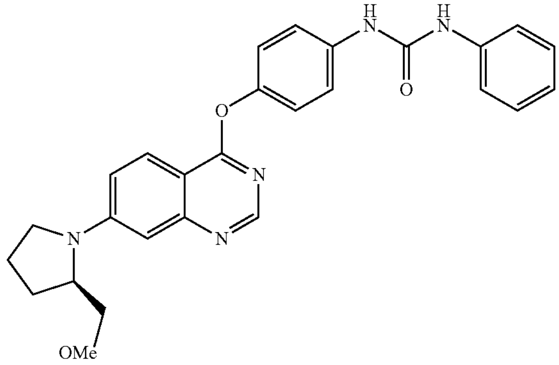 [SMILES: COC[C@H]1CCCN1c1ccc2c(Oc3ccc(NC(=O)Nc4ccccc4)cc3)ncnc2c1] | 469 | 470 |
| 11 | 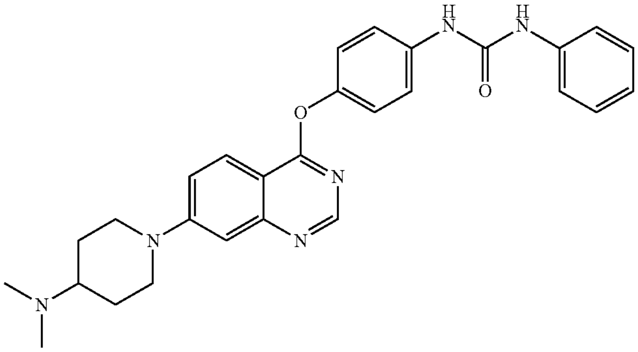 [SMILES: CN(C)C1CCN(c2ccc3c(Oc4ccc(NC(=O)Nc5ccccc5)cc4)ncnc3c2)CC1] | 482 | 483 |
| 12 | 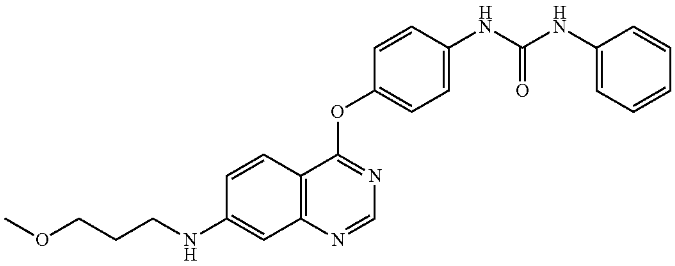 [SMILES: COCCCNc1ccc2c(Oc3ccc(NC(=O)Nc4ccccc4)cc3)ncnc2c1] | 443 | 444 |
| 13 | 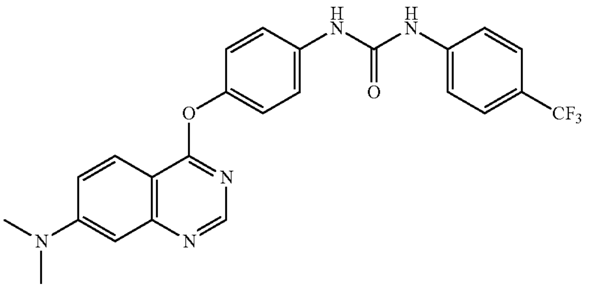 [SMILES: CN(C)c1ccc2c(Oc3ccc(NC(=O)Nc4ccc(C(F)(F)F)cc4)cc3)ncnc2c1] | 467 | 468 |

TABLE 1-continued
Exemplary heterocyclic compounds
| Compound | Structure | Calculated Mass | Mass [M + H]+ |
|---|---|---|---|
| 14 | 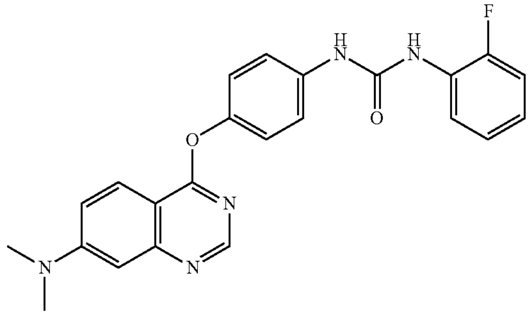 [SMILES: CN(C)c1ccc2c(Oc3ccc(NC(=O)Nc4ccccc4F)cc3)ncnc2c1] | 417 | 418 |
| 15 | 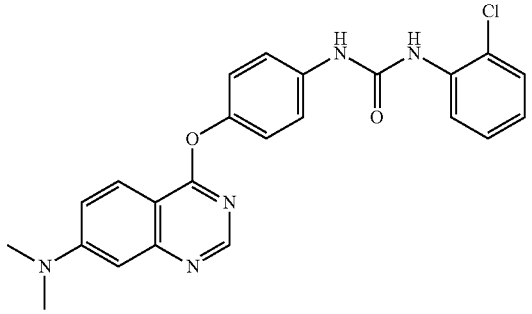 | 433 | 434 |
| 16 | 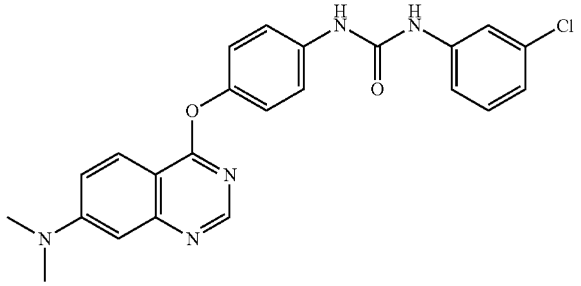 [SMILES: CN(C)c1ccc2c(Oc3ccc(NC(=O)Nc4cccc(Cl)c4)cc3)ncnc2c1] | 433 | 434 |
| 17 | 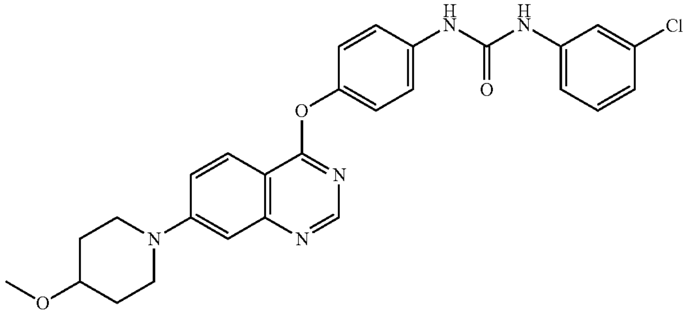 [SMILES: COC1CCN(c2ccc3c(Oc4ccc(NC(=O)Nc5cccc(Cl)c5)cc4)ncnc3c2)CC1] | 503 | 504 |
| 18 | 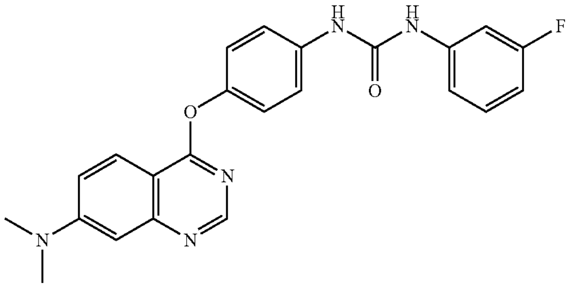 [SMILES: CN(C)c1ccc2c(Oc3ccc(NC(=O)Nc4cccc(F)c4)cc3)ncnc2c1] | 417 | 418 |

TABLE 1-continued
| Exemplary heterocyclic compounds | | | |
|---|---|---|---|
| Compound | Structure | Calculated Mass | Mass [M + H]$^+$ |
| 19 | 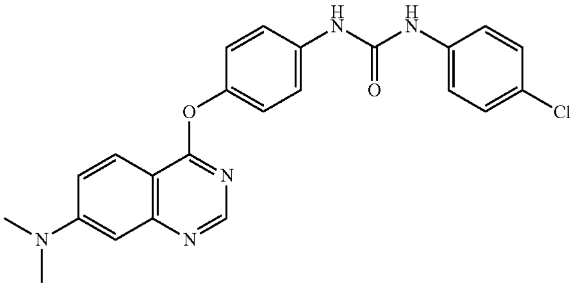 [SMILES: CN(C)c1ccc2c(Oc3ccc(NC(=O)Nc4ccc(Cl)cc4)cc3)ncnc2c1] | 433 | 434 |
| 20 | 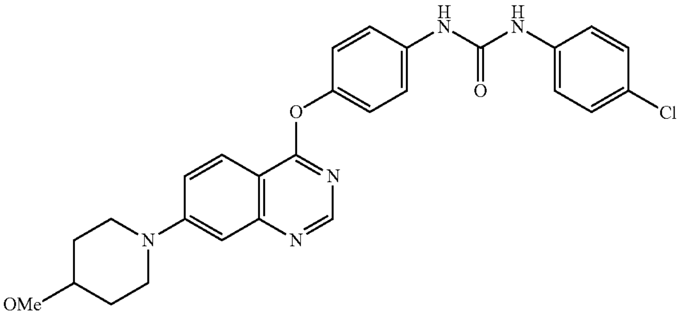 [SMILES: COC1CCN(c2ccc3c(Oc4ccc(NC(=O)Nc5ccc(Cl)cc5)cc4)ncnc3c2)CC1] | 503 | 504 |
| 21 | 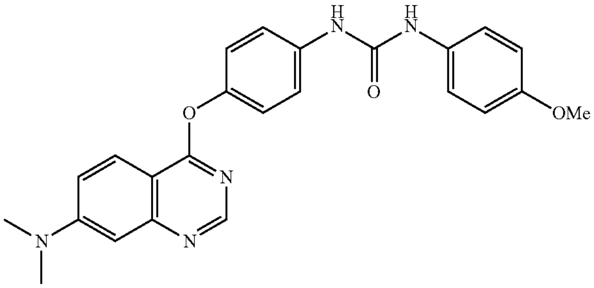 [SMILES: COc1ccc(NC(=O)Nc2ccc(Oc3ncnc4cc(N(C)C)ccc34)cc2)cc1] | 429 | 430 |
| 22 | 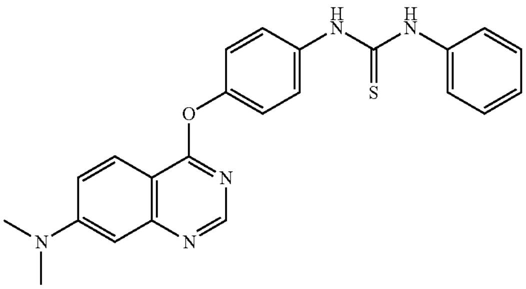 | 415 | 416 |

TABLE 1-continued
| Exemplary heterocyclic compounds | | | |
|---|---|---|---|
| Compound | Structure | Calculated Mass | Mass [M + H]+ |
| 23 | 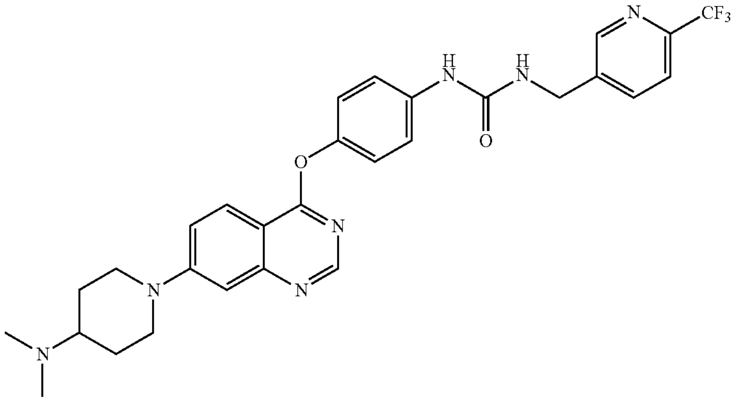 [SMILES: CN(C)C1CCN(c2ccc3c(Oc4ccc(NC(=O)NCc5ccc(C(F)(F)F)nc5)cc4)ncnc3c2)CC1] | 565 | 566 |
| 24 | 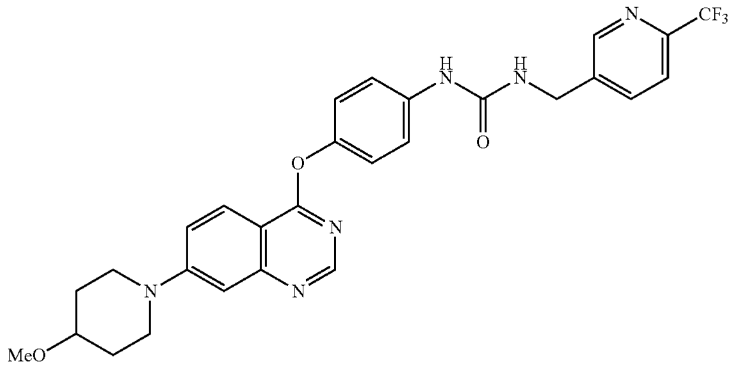 [SMILES: COC1CCN(c2ccc3c(Oc4ccc(NC(=O)NCc5ccc(C(F)(F)F)nc5)cc4)ncnc3c2)CC1] | 552 | 553 |
| 25 | 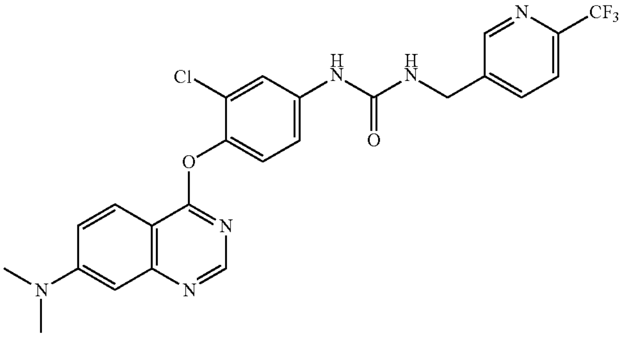 [SMILES: CN(C)c1ccc2c(Oc3ccc(NC(=O)NCc4ccc(C(F)(F)F)nc4)cc3Cl)ncnc2c1] | 516 | 517 |
| 26 | 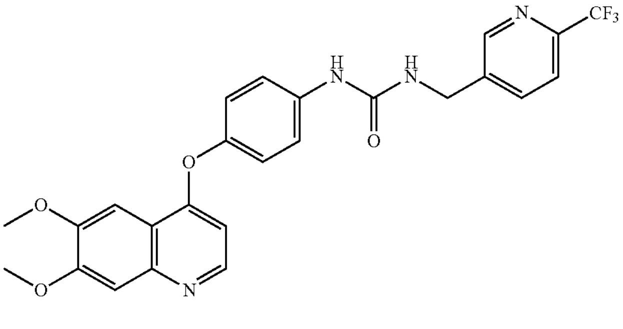 [SMILES: COc1cc2nccc(Oc3ccc(NC(=O)NCc4ccc(C(F)(F)F)nc4)cc3)c2cc1OC] | 498 | 499 |

TABLE 1-continued
| Exemplary heterocyclic compounds | | | |
|---|---|---|---|
| Compound | Structure | Calculated Mass | Mass [M + H]+ |
| 27 | 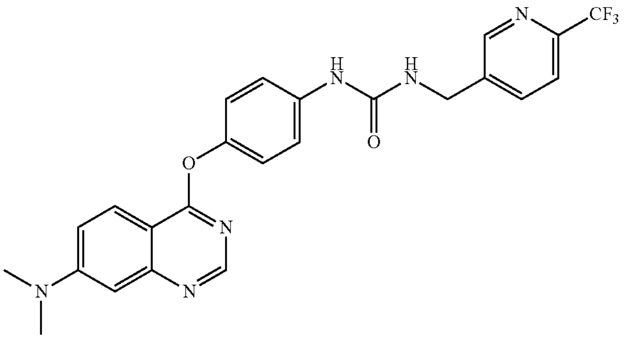 [SMILES: CN(C)c1ccc2c(Oc3ccc(NC(=O)NCc4ccc(C(F)(F)F)nc4)cc3)ncnc2c1] | 482 | 483 |
| 28 | 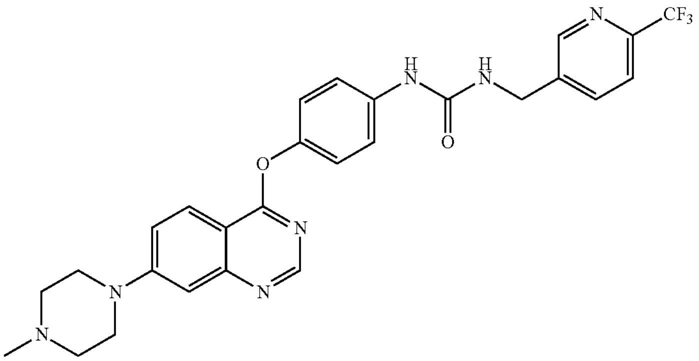 [SMILES: CN1CCN(c2ccc3c(Oc4ccc(NC(=O)NCc5ccc(C(F)(F)F)nc5)cc4)ncnc3c2)CC1] | 537 | 538 |
| 29 | 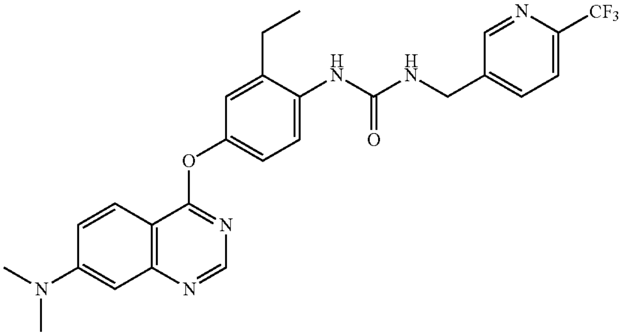 [SMILES: CCc1cc(Oc2ncnc3cc(N(C)C)ccc23)ccc1NC(=O)NCc1ccc(C(F)(F)F)nc1] | 510 | 511 |
| 30 | 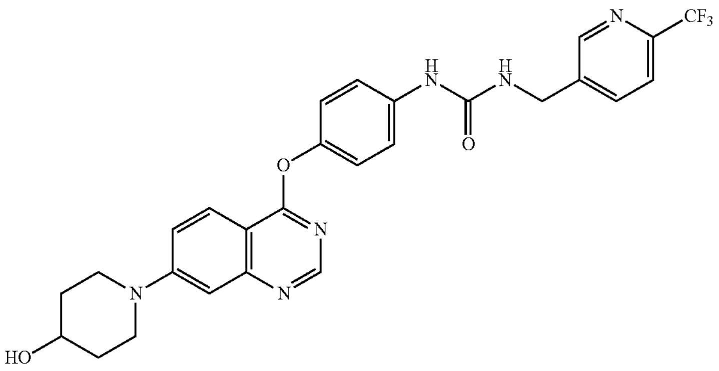 [SMILES: O=C(NCc1ccc(C(F)(F)F)nc1)Nc1ccc(Oc2ncnc3cc(N4CCC(O)CC4)ccc23)cc1] | 538 | 539 |

TABLE 1-continued
| Exemplary heterocyclic compounds | | | |
|---|---|---|---|
| Compound | Structure | Calculated Mass | Mass [M + H]+ |
| 31 | 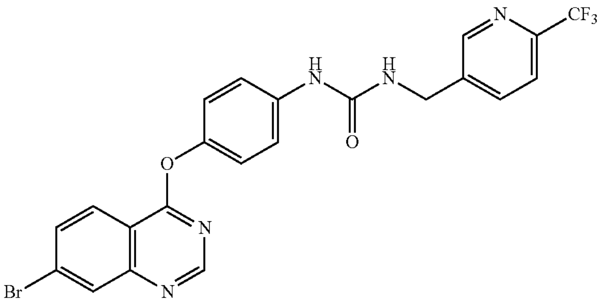 [SMILES: O=C(NCc1ccc(C(F)(F)F)nc1)Nc1ccc(Oc2ncnc3cc(Br)ccc23)cc1] | 517 | 518 |
| 32 | 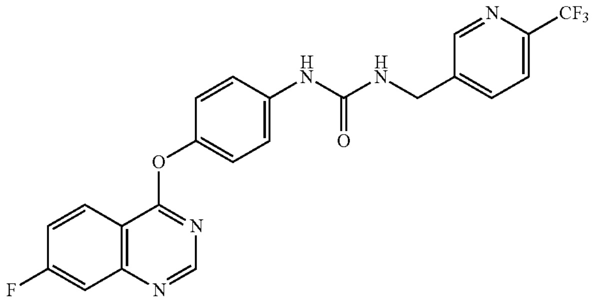 [SMILES: O=C(NCc1ccc(C(F)(F)F)nc1)Nc1ccc(Oc2ncnc3cc(F)ccc23)cc1] | 457 | 458 |
| 33 | 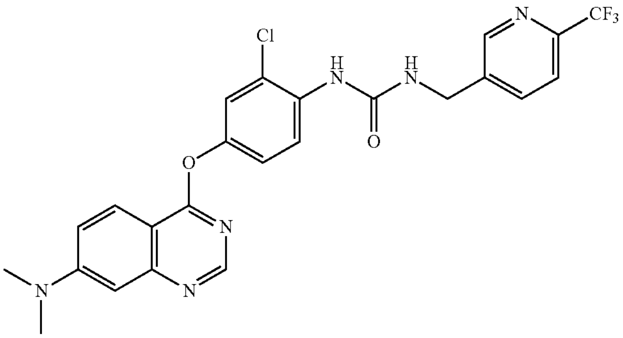 [SMILES: CN(C)c1ccc2c(Oc3ccc(NC(=O)NCc4ccc(C(F)(F)F)nc4)c(Cl)c3)ncnc2c1] | 516 | 517 |
| 34 | 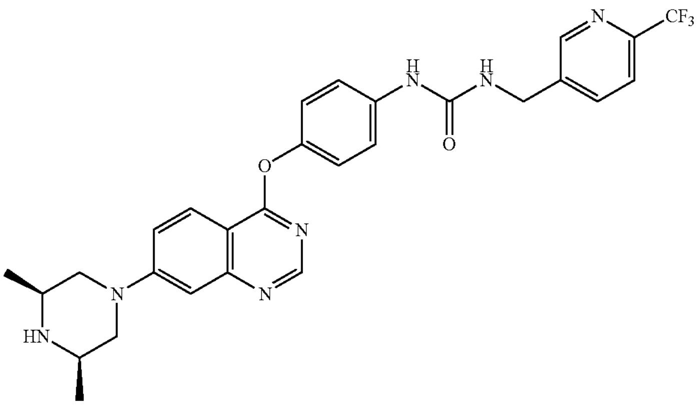 [SMILES: C[C@@H]1CN(c2ccc3c(Oc4ccc(NC(=O)NCc5ccc(C(F)(F)F)nc5)cc4)ncnc3c2)C[C@H](C)N1] | 551 | 552 |

TABLE 1-continued
| Exemplary heterocyclic compounds | | | |
|---|---|---|---|
| Compound | Structure | Calculated Mass | Mass $[M + H]^+$ |
| 35 | 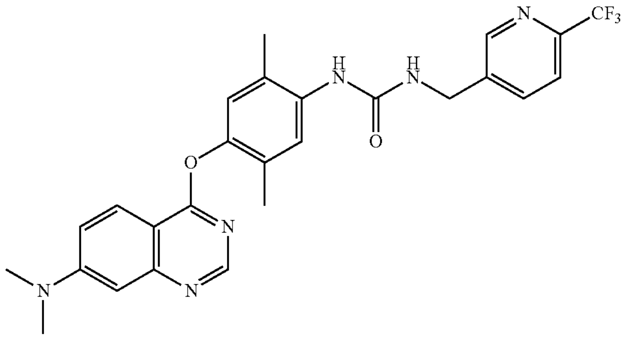 [SMILES: Cc1cc(Oc2ncnc3cc(N(C)C)ccc23)c(C)cc1NC(=O)NCc1ccc(C(F)(F)F)nc1] | 510 | 511 |
| 36 | 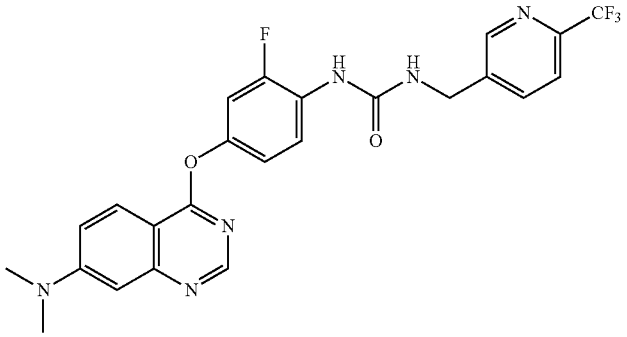 [SMILES: CN(C)c1ccc2c(Oc3ccc(NC(=O)NCc4ccc(C(F)(F)F)nc4)c(F)c3)ncnc2c1] | 500 | 501 |
| 37 | 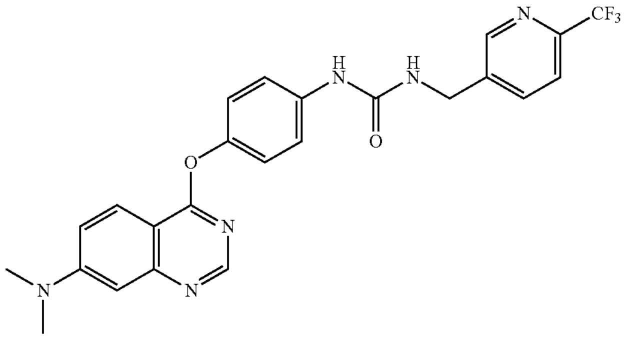 [SMILES: CN(C)c1ccc2c(Oc3ccc(NC(=O)NCc4ccc(C(F)(F)F)nc4)cc3)ncnc2c1] | 498 | 499 |
| 38 | 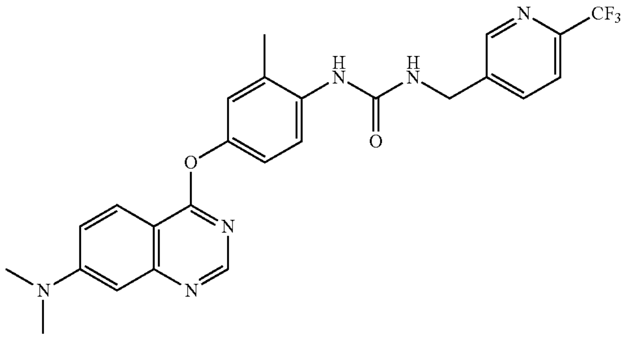 [SMILES: Cc1cc(Oc2ncnc3cc(N(C)C)ccc23)ccc1NC(=O)NCc1ccc(C(F)(F)F)nc1] | 496 | 497 |

TABLE 1-continued
| Exemplary heterocyclic compounds | | | |
|---|---|---|---|
| Compound | Structure | Calculated Mass | Mass [M + H]+ |
| 39 | 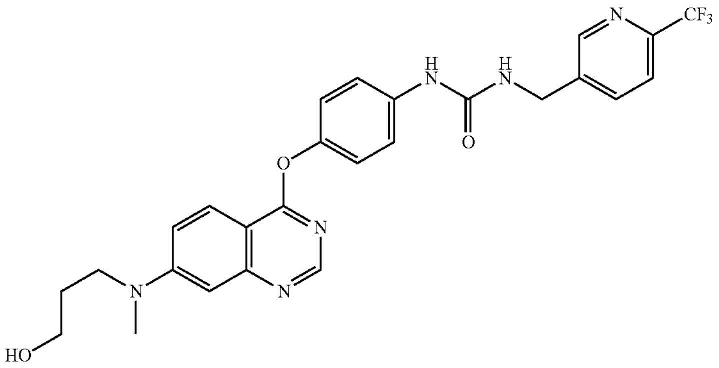 [SMILES: CN(CCCO)c1ccc2c(Oc3ccc(NC(=O)NCc4ccc(C(F)(F)F)nc4)cc3)ncnc2c1] | 526 | 527 |
| 40 | 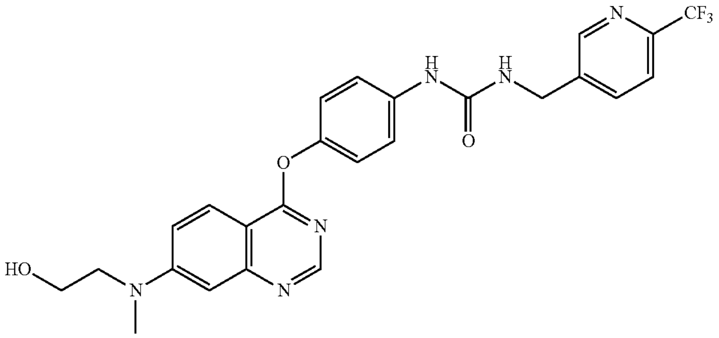 [SMILES: CN(CCO)c1ccc2c(Oc3ccc(NC(=O)NCc4ccc(C(F)(F)F)nc4)cc3)ncnc2c1] | 512 | 513 |
| 41 | 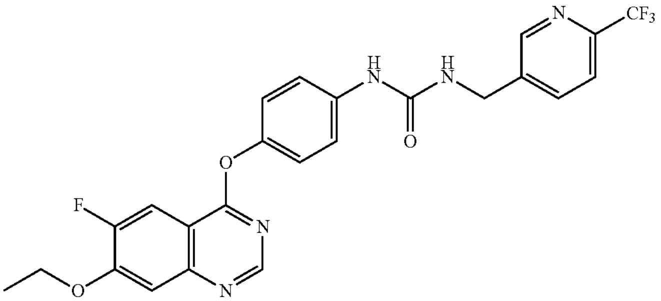 [SMILES: CCOc1cc2ncnc(Oc3ccc(NC(=O)NCc4ccc(C(F)(F)F)nc4)cc3)c2cc1F] | 501 | 502 |
| 42 | 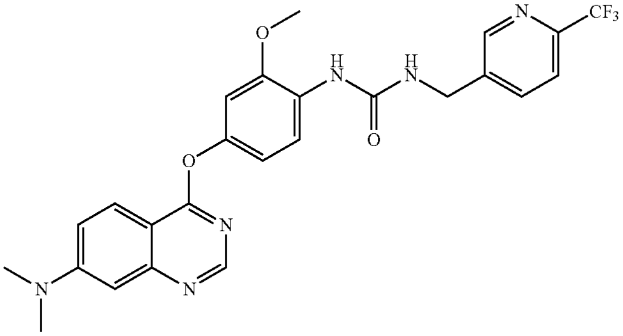 [SMILES: COc1cc(Oc2ncnc3cc(N(C)C)ccc23)ccc1NC(=O)NCc1ccc(C(F)(F)F)nc1] | 512 | 513 |

TABLE 1-continued
| Exemplary heterocyclic compounds | | | |
|---|---|---|---|
| Compound | Structure | Calculated Mass | Mass [M + H]+ |
| 43 | 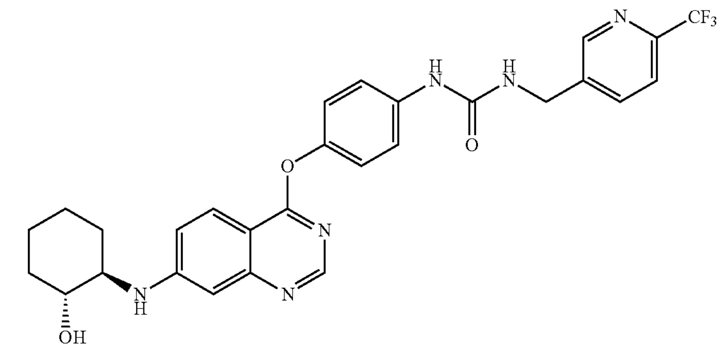 [SMILES: O=C(NCc1ccc(C(F)(F)F)nc1)Nc1ccc(Oc2ncnc3cc(N[C@@H]4CCCC[C@H]4O)ccc23)cc1] | 552 | 553 |
| 44 | 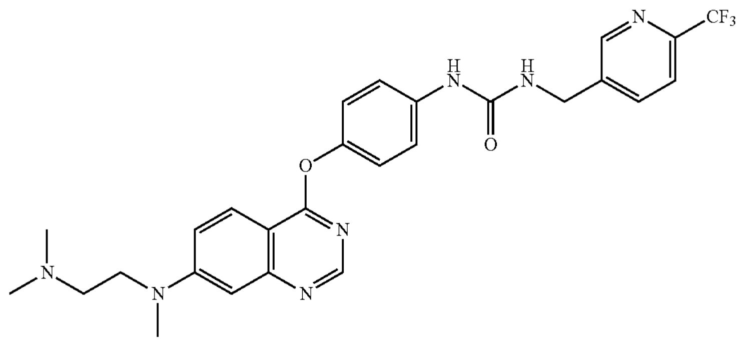 [SMILES: CN(C)CCN(C)c1ccc2c(Oc3ccc(NC(=O)NCc4ccc(C(F)(F)F)nc4)cc3)ncnc2c1] | 539 | 540 |
| 45 | 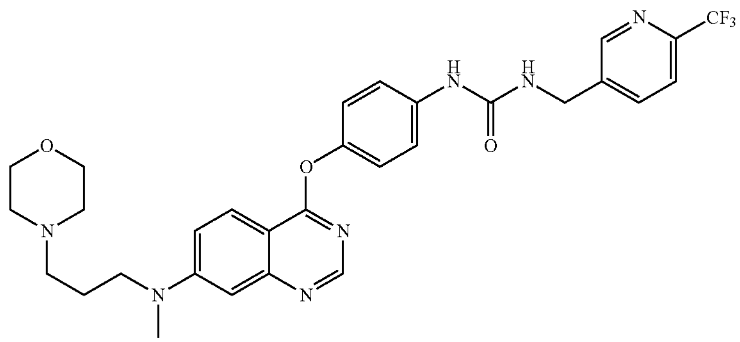 [SMILES: CN(CCCN1CCOCC1)c1ccc2c(Oc3ccc(NC(=O)NCc4ccc(C(F)(F)F)nc4)cc3)ncnc2c1] | 595 | 596 |
| 46 | 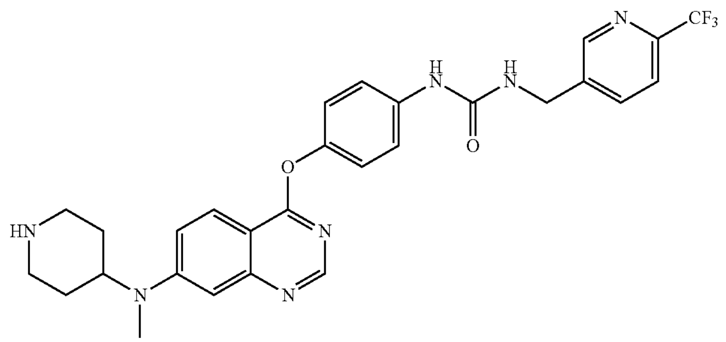 [SMILES: CN(c1ccc2c(Oc3ccc(NC(=O)NCc4ccc(C(F)(F)F)nc4)cc3)ncnc2c1)C1CCNCC1] | 551 | 552 |

TABLE 1-continued
| Exemplary heterocyclic compounds | | | |
|---|---|---|---|
| Compound | Structure | Calculated Mass | Mass [M + H]$^+$ |
| 47 | 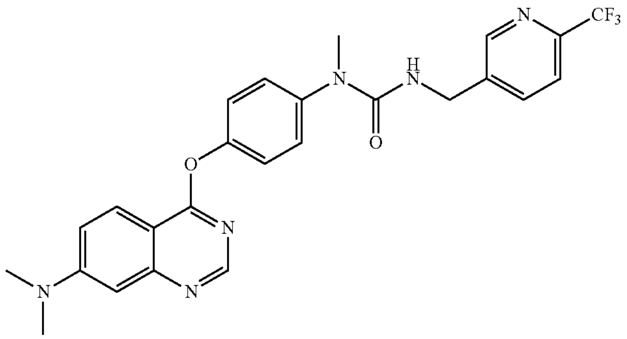 [SMILES: CN(C)c1ccc2c(Oc3ccc(N(C)C(=O)NCc4ccc(C(F)(F)F)nc4)cc3)ncnc2c1] | 496 | 497 |
| 48 | 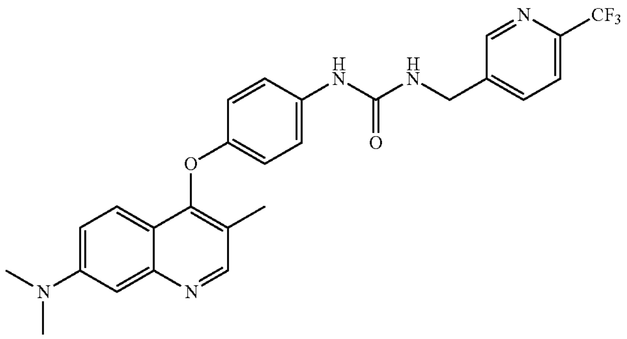 [SMILES: Cc1cnc2cc(N(C)C)ccc2c1Oc1ccc(NC(=O)NCc2ccc(C(F)(F)F)nc2)cc1] | 495 | 496 |
| 49 | 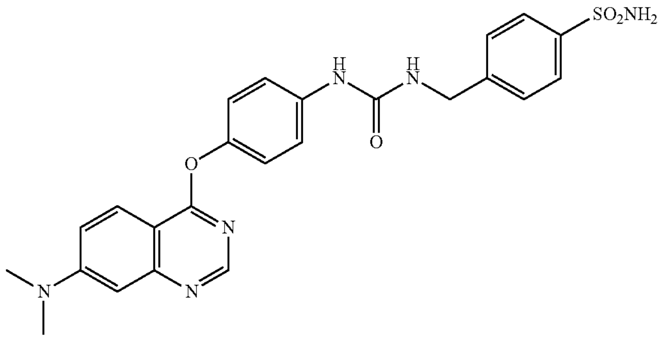 [SMILES: CN(C)c1ccc2c(Oc3ccc(NC(=O)NCc4ccc(S(N)(=O)=O)cc4)cc3)ncnc2c1] | 492 | 493 |
| 50 | 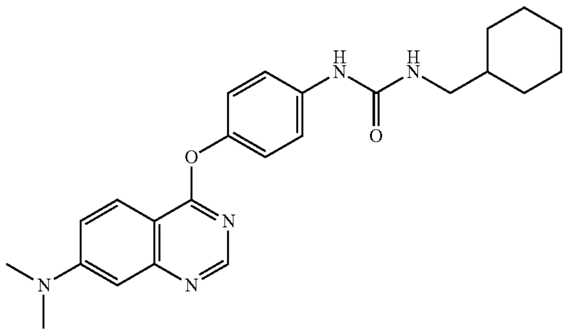 [SMILES: CN(C)c1ccc2c(Oc3ccc(NC(=O)NCC4CCCCC4)cc3)ncnc2c1] | 419 | 420 |

TABLE 1-continued
| Exemplary heterocyclic compounds | | | |
|---|---|---|---|
| Compound | Structure | Calculated Mass | Mass $[M + H]^+$ |
| 51 | 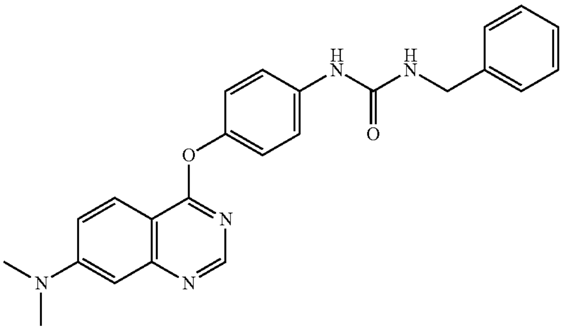 [SMILES: CN(C)c1ccc2c(Oc3ccc(NC(=O)NCc4ccccc4)cc3)ncnc2c1] | 413 | 414 |
| 52 | 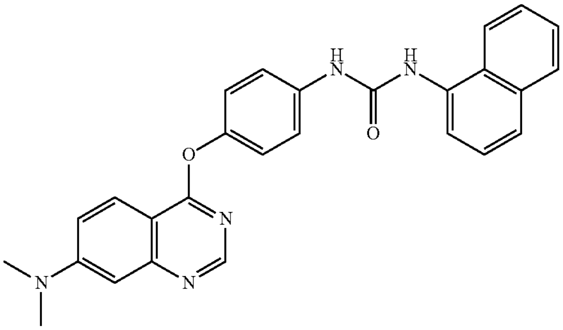 [SMILES: CN(C)c1ccc2c(Oc3ccc(NC(=O)Nc4cccc5ccccc45)cc3)ncnc2c1] | 449 | 450 |
| 53 | 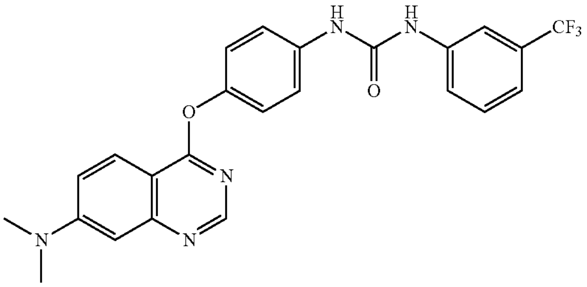 [SMILES: CN(C)c1ccc2c(Oc3ccc(NC(=O)Nc4cccc(C(F)(F)F)c4)cc3)ncnc2c1] | 467 | 468 |
| 54 | 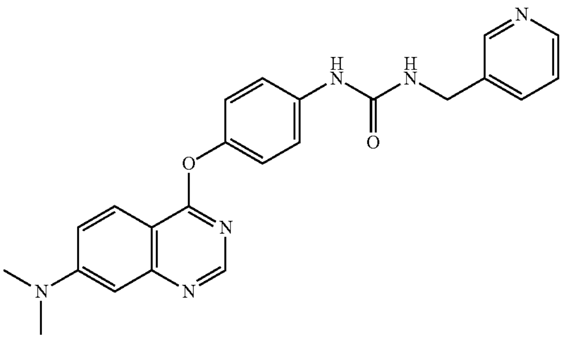 [SMILES: CN(C)c1ccc2c(Oc3ccc(NC(=O)NCc4cccnc4)cc3)ncnc2c1] | 414 | 415 |

TABLE 1-continued
| Exemplary heterocyclic compounds | | | |
|---|---|---|---|
| Compound | Structure | Calculated Mass | Mass $[M + H]^+$ |
| 55 | 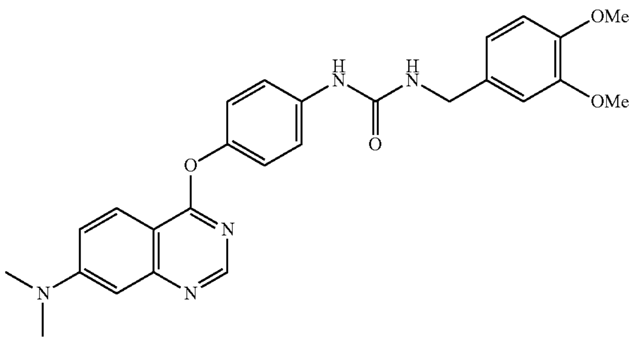 [SMILES: COc1ccc(CNC(=O)Nc2ccc(Oc3ncnc4cc(N(C)C)ccc34)cc2)cc1OC] | 473 | 474 |
| 56 | 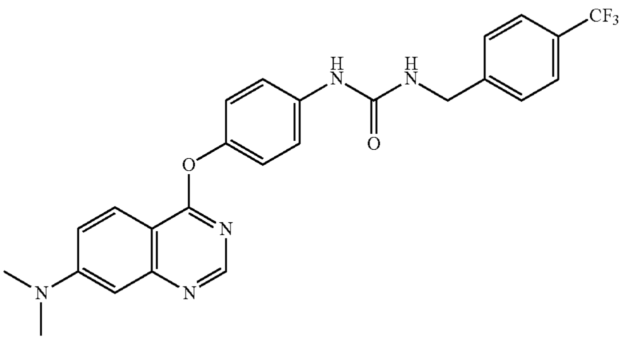 [SMILES: CN(C)c1ccc2c(Oc3ccc(NC(=O)NCc4ccc(C(F)(F)F)cc4)cc3)ncnc2c1] | 481 | 482 |
| 57 | 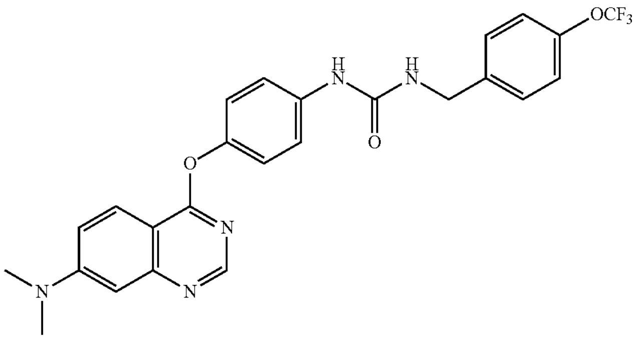 [SMILES: CN(C)c1ccc2c(Oc3ccc(NC(=O)NCc4ccc(OC(F)(F)F)cc4)cc3)ncnc2c1] | 497 | 498 |
| 58 | 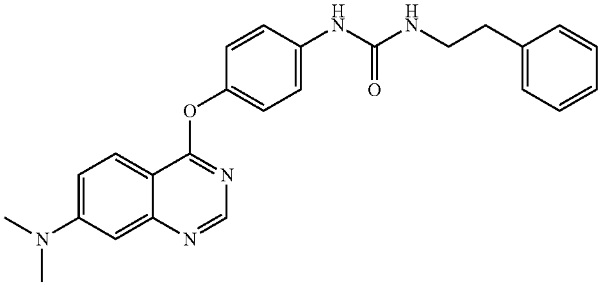 [SMILES: CN(C)c1ccc2c(Oc3ccc(NC(=O)NCCc4ccccc4)cc3)ncnc2c1] | 427 | 428 |

TABLE 1-continued
| Exemplary heterocyclic compounds | | | |
|---|---|---|---|
| Compound | Structure | Calculated Mass | Mass $[M + H]^+$ |
| 59 | 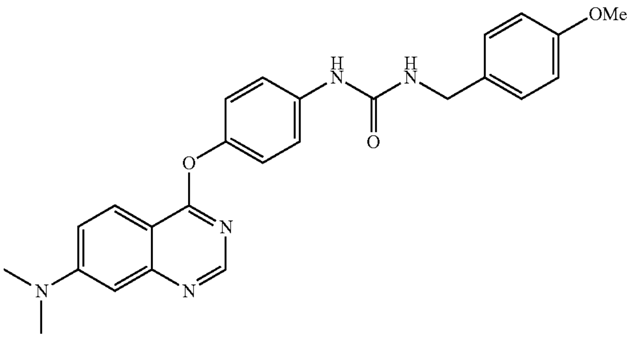 [SMILES: COc1ccc(CNC(=O)Nc2ccc(Oc3ncnc4cc(N(C)C)ccc34)cc2)cc1] | 443 | 444 |
| 60 | 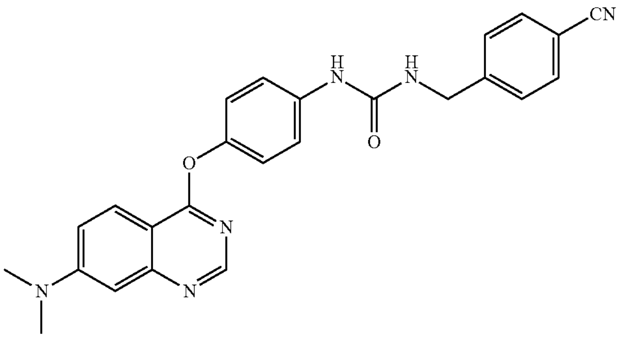 [SMILES: CN(C)c1ccc2c(Oc3ccc(NC(=O)NCc4ccc(C#N)cc4)cc3)ncnc2c1] | 438 | 439 |
| 61 | 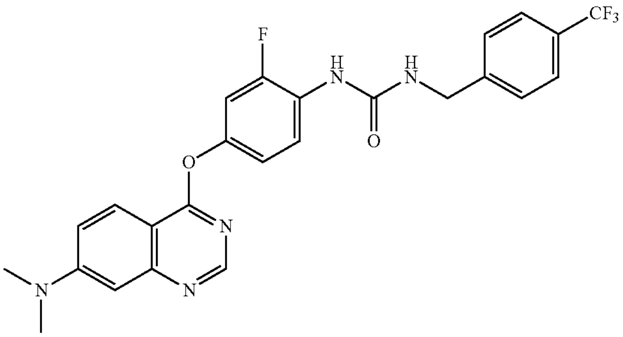 [SMILES: CN(C)c1ccc2c(Oc3ccc(NC(=O)NCc4ccc(C(F)(F)F)cc4)c(F)c3)ncnc2c1] | 499 | 500 |
| 62 | 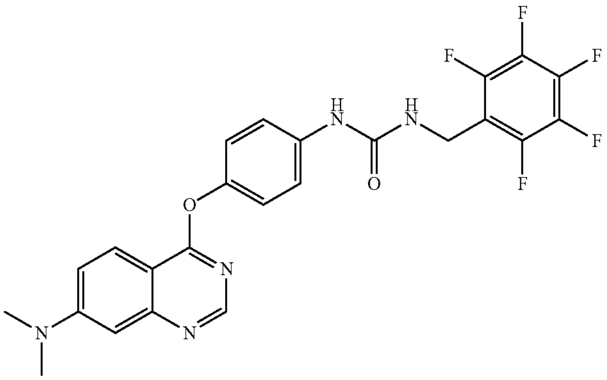 [SMILES: CN(C)c1ccc2c(Oc3ccc(NC(=O)NCc4c(F)c(F)c(F)c(F)c4F)cc3)ncnc2c1] | 503 | 504 |

TABLE 1-continued
| Exemplary heterocyclic compounds | | | |
|---|---|---|---|
| Compound | Structure | Calculated Mass | Mass [M + H]+ |
| 63 | 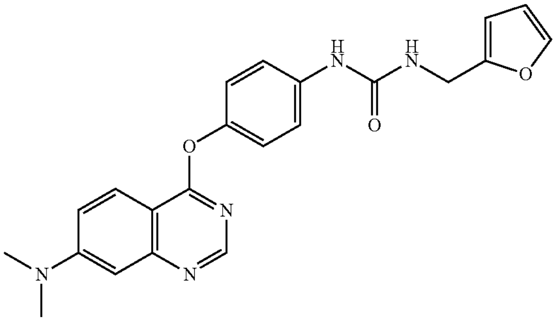 [SMILES: CN(C)c1ccc2c(Oc3ccc(NC(=O)NCc4ccco4)cc3)ncnc2c1] | 403 | 404 |
| 64 | 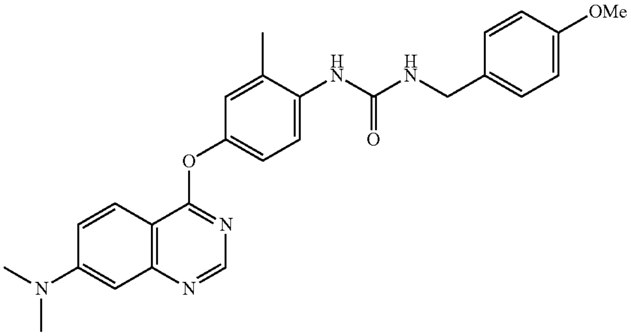 [SMILES: COc1ccc(CNC(=O)Nc2ccc(Oc3ncnc4cc(N(C)C)ccc34)cc2C)cc1] | 457 | 458 |
| 65 | 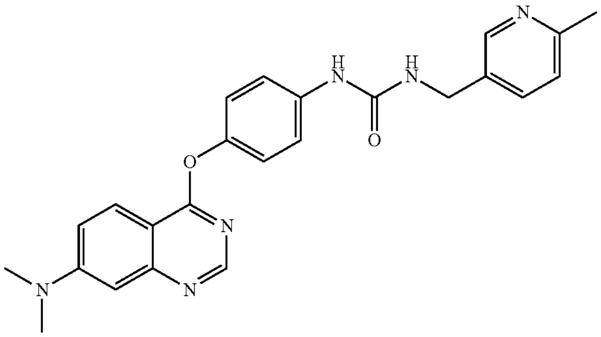 | 428 | 429 |
| 66 | 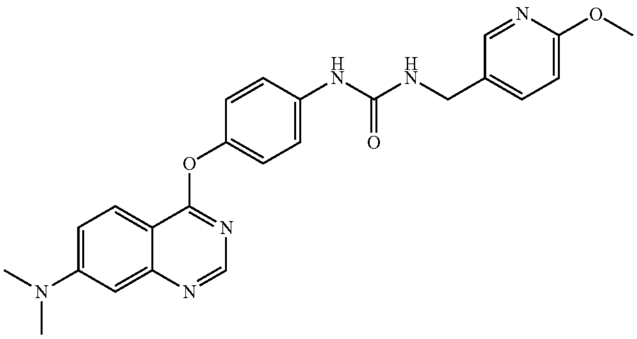 | 444 | 445 |

TABLE 1-continued
| Exemplary heterocyclic compounds | | | |
|---|---|---|---|
| Compound | Structure | Calculated Mass | Mass [M + H]+ |
| 67 | 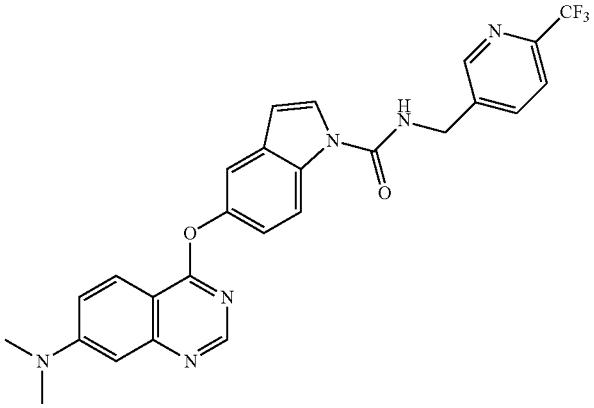 [SMILES: CN(C)c1ccc2c(Oc3ccc4c(ccn4C(=O)NCc4ccc(C(F)(F)F)nc4)c3)ncnc2c1] | 506 | 507 |
| 68 | 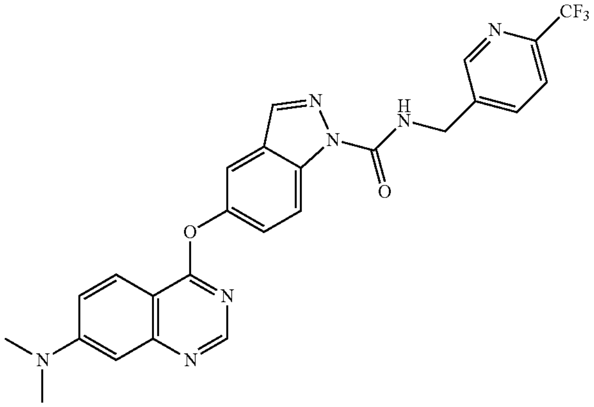 [SMILES: CN(C)c1ccc2c(Oc3ccc4c(cnn4C(=O)NCc4ccc(C(F)(F)F)nc4)c3)ncnc2c1] | 507 | 508 |
| 69 | 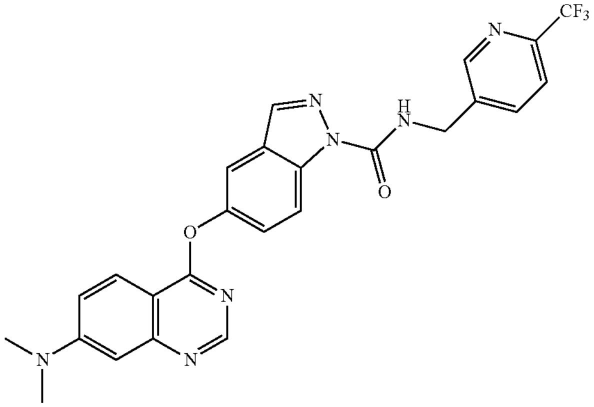 [SMILES: CN(C)c1ccc2c(Oc3ccc4c(cnn4C(=O)NCc4ccc(C(F)(F)F)nc4)c3)ncnc2c1] | 507 | 508 |
| 71 | 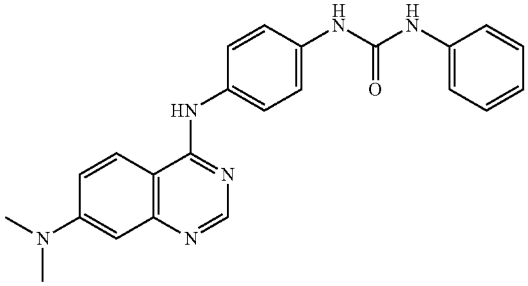 [SMILES: CN(C)c1ccc2c(Nc3ccc(NC(=O)Nc4ccccc4)cc3)ncnc2c1] | 398 | 399 |

TABLE 1-continued
Exemplary heterocyclic compounds
| Compound | Structure | Calculated Mass | Mass $[M + H]^+$ |
|---|---|---|---|
| 72 | 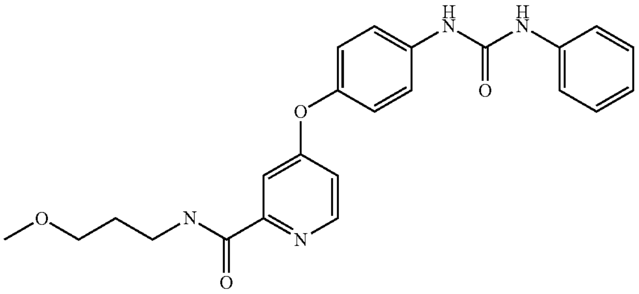 [SMILES: COCCCNC(=O)c1cc(Oc2ccc(NC(=O)Nc3ccccc3)cc2)ccn1] | 420 | 421 |
| 73 | 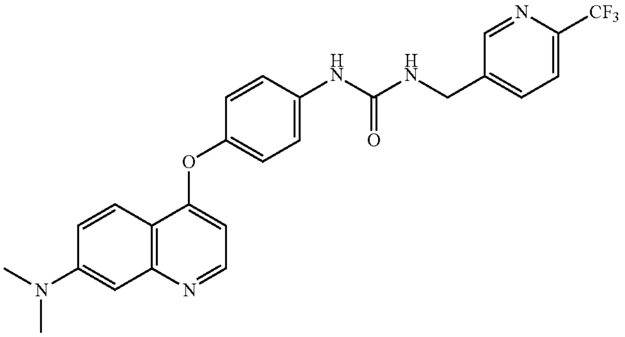 [SMILES: CN(C)c1ccc2c(Oc3ccc(NC(=O)NCc4ccc(C(F)(F)F)nc4)cc3)ccnc2c1] | 481 | 482 |
| 74 | 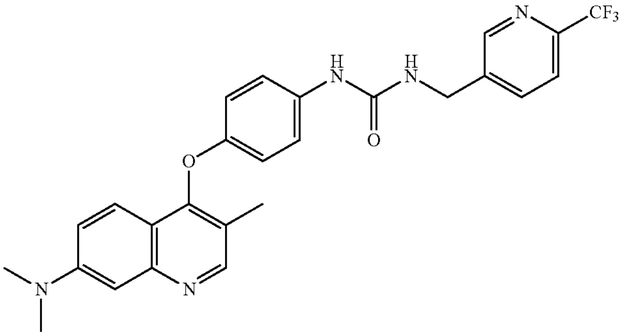 [SMILES: Cc1cnc2cc(N(C)C)ccc2c1Oc1ccc(NC(=O)NCc2ccc(C(F)(F)F)nc2)cc1] | 495 | 496 |
| 75 | 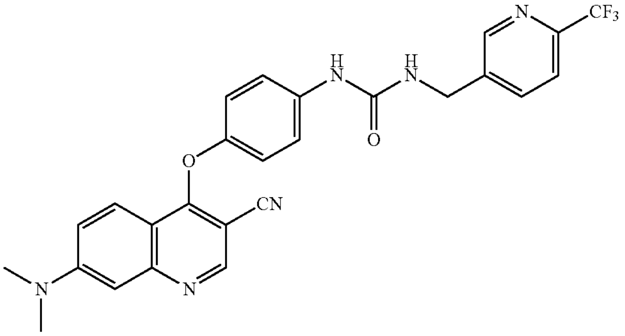 [SMILES: CN(C)c1ccc2c(Oc3ccc(NC(=O)NCc4ccc(C(F)(F)F)nc4)cc3)c(C#N)cnc2c1] | 506 | 507 |

TABLE 1-continued
| Exemplary heterocyclic compounds | | | |
|---|---|---|---|
| Compound | Structure | Calculated Mass | Mass [M + H]+ |
| 76 | 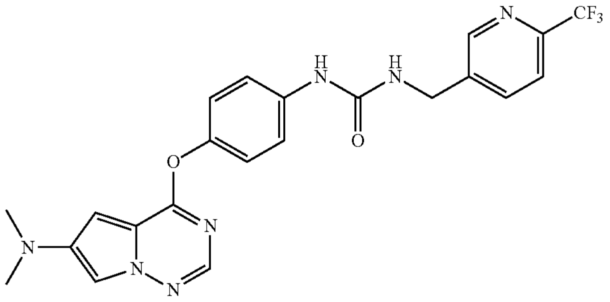 [SMILES: CN(C)c1cc2c(Oc3ccc(NC(=O)NCc4ccc(C(F)(F)F)nc4)cc3)ncnn2c1] | 471 | 472 |
| 77 | 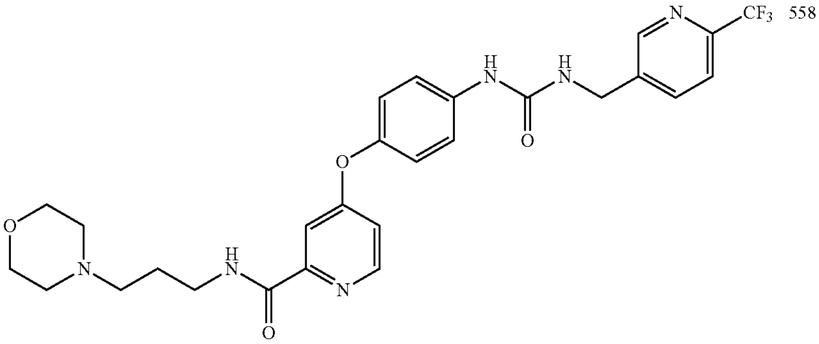 | 558 | 559 |
| 78 | 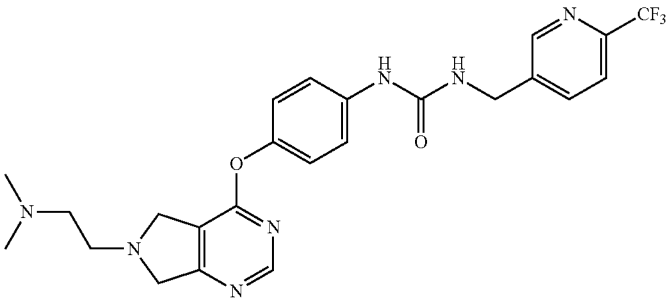 [SMILES: CN(C)CCN1Cc2ncnc(Oc3ccc(NC(=O)NCc4ccc(C(F)(F)F)nc4)cc3)c2C1] | 503 | 504 |
| 79 | 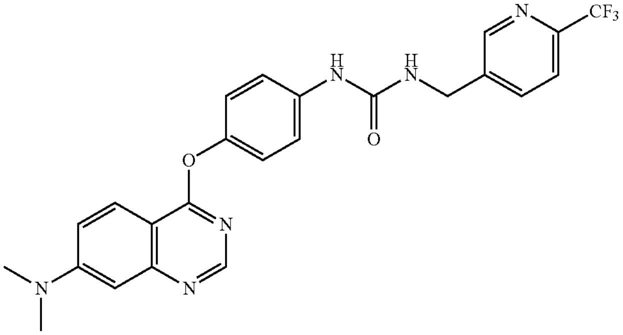 [SMILES: CN(C)c1ccc2c(Oc3ccc(NC(=O)NCc4ccc(C(F)(F)F)nc4)cc3)ncnc2c1] | 481 | 482 |

TABLE 1-continued
| Exemplary heterocyclic compounds | | | |
|---|---|---|---|
| Compound | Structure | Calculated Mass | Mass [M + H]+ |
| 80 | 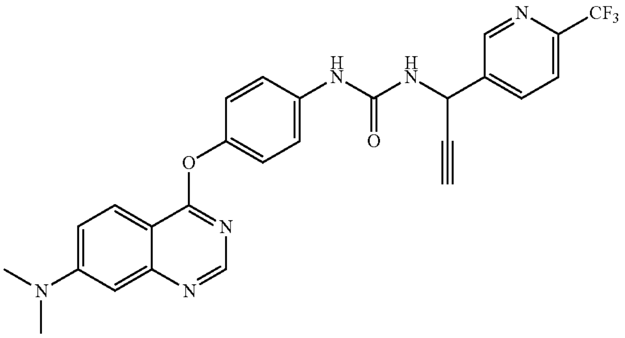 [SMILES: C#CC(NC(=O)Nc1ccc(Oc2ncnc3cc(N(C)C)ccc23)cc1)c1ccc(C(F)(F)F)nc1] | 506 | 507 |
| 81 | 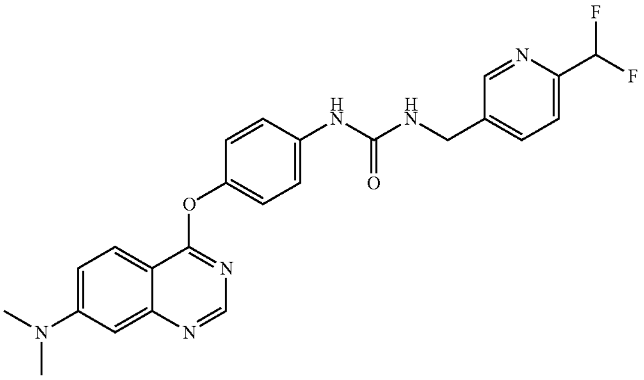 [SMILES: CN(C)c1ccc2c(Oc3ccc(NC(=O)NCc4ccc(C(F)F)nc4)cc3)ncnc2c1] | 464 | 465 |
| 82 | 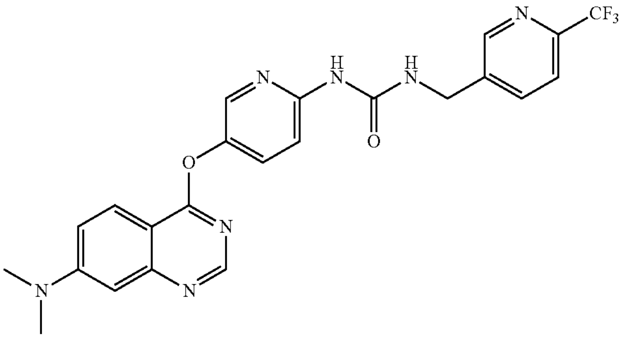 [SMILES: CN(C)c1ccc2c(Oc3ccc(NC(=O)NCc4ccc(C(F)(F)F)nc4)nc3)ncnc2c1] | 483 | 484 |
| 83 | 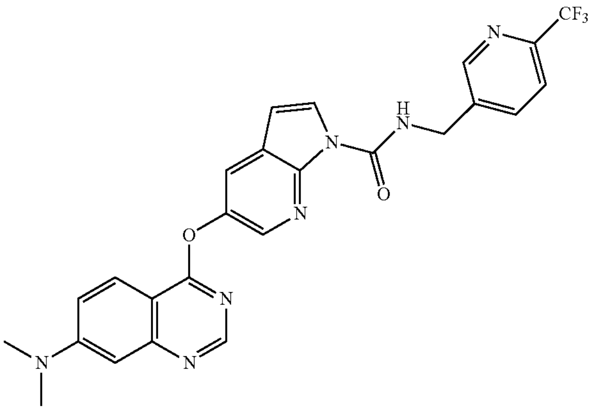 [SMILES: CN(C)c1ccc2c(Oc3cnc4c(ccn4C(=O)NCc4ccc(C(F)(F)F)nc4)c3)ncnc2c1] | 507 | 508 |

TABLE 1-continued
| Exemplary heterocyclic compounds | | | |
|---|---|---|---|
| Compound | Structure | Calculated Mass | Mass [M + H]+ |
| 84 | 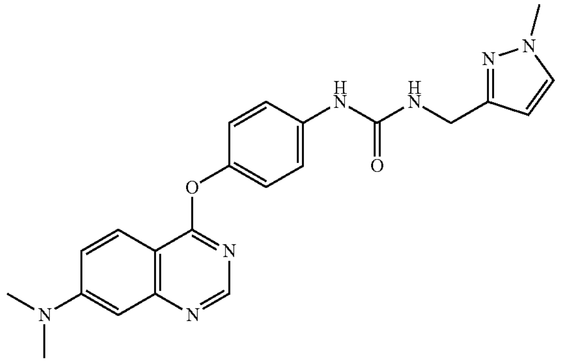 [SMILES: CN(C)c1ccc2c(Oc3ccc(NC(=O)NCc4ccn(C)n4)cc3)ncnc2c1] | 417 | 418 |
| 85 | 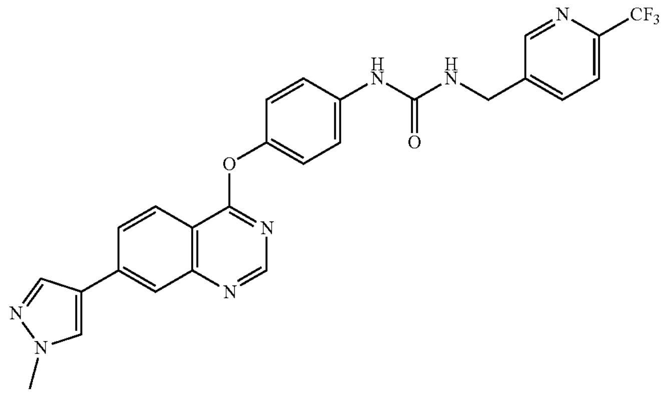 [SMILES: Cn1cc(-c2ccc3c(Oc4ccc(NC(=O)NCc5ccc(C(F)(F)F)nc5)cc4)ncnc3c2)cn1] | 519 | 520 |
| 86 | 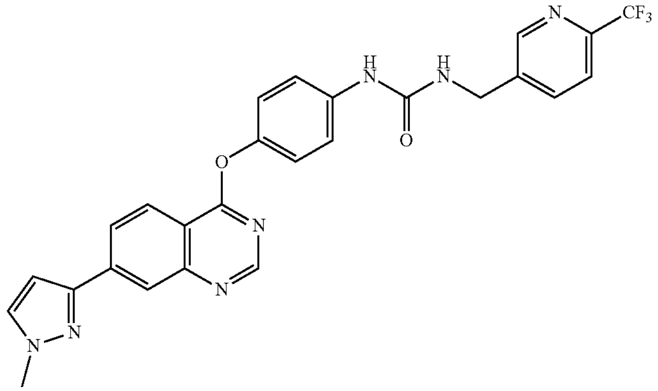 [SMILES: Cn1ccc(-c2ccc3c(Oc4ccc(NC(=O)NCc5ccc(C(F)(F)F)nc5)cc4)ncnc3c2)n1] | 519 | 520 |
| 87 | 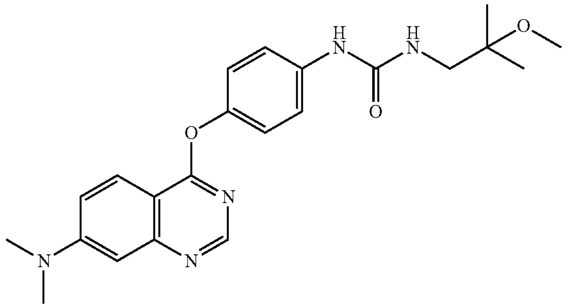 | 409 | 410 |

TABLE 1-continued
| Exemplary heterocyclic compounds | | | |
|---|---|---|---|
| Compound | Structure | Calculated Mass | Mass $[M + H]^+$ |
| 88 | 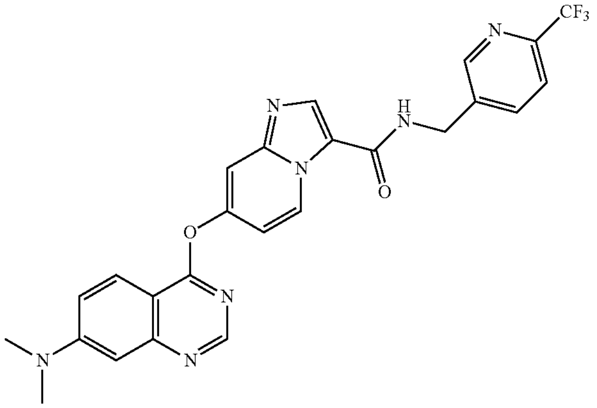 [SMILES: CN(C)c1ccc2c(Oc3ccn4c(C(=O)NCc5ccc(C(F)(F)F)nc5)cnc4c3)ncnc2c1] | 507 | 508 |
| 89 | 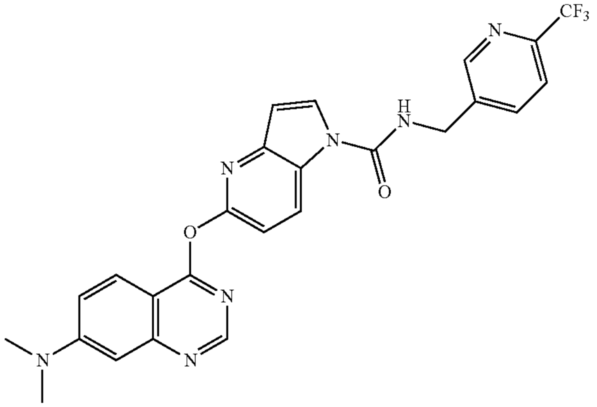 [SMILES: CN(C)c1ccc2c(Oc3ccc4c(ccn4C(=O)NCc4ccc(C(F)(F)F)nc4)n3)ncnc2c1] | 507 | 508 |
| 90 | 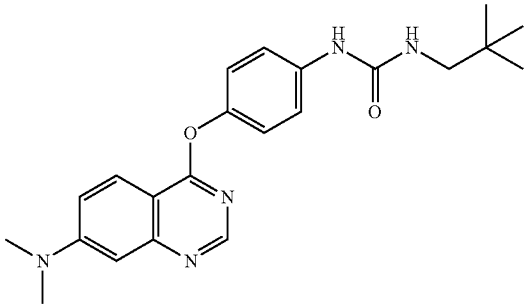 [SMILES: CN(C)c1ccc2c(Oc3ccc(NC(=O)NCC(C)(C)C)cc3)ncnc2c1] | 393 | 394 |
| 91 | 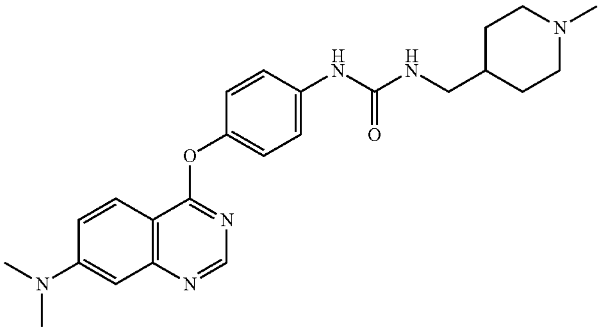 | 434 | 435 |

TABLE 1-continued
| Exemplary heterocyclic compounds | | | |
|---|---|---|---|
| Compound | Structure | Calculated Mass | Mass [M + H]+ |
| 92 | 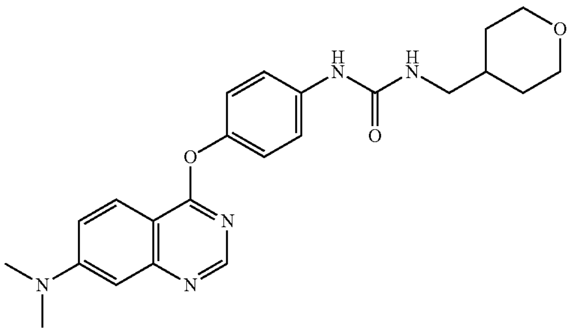 [SMILES: CN(C)c1ccc2c(Oc3ccc(NC(=O)NCC4CCOCC4)cc3)ncnc2c1] | 421 | 422 |
| 93 | 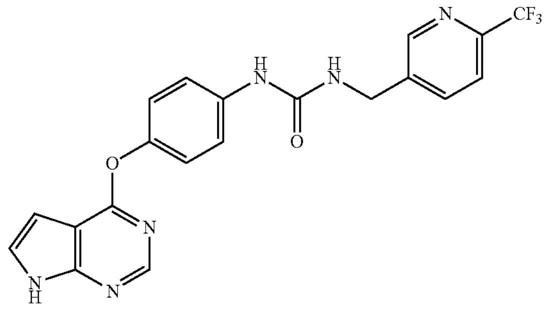 [SMILES: O=C(NCc1ccc(C(F)(F)F)nc1)Nc1ccc(Oc2ncnc3[nH]ccc23)cc1] | 428 | 429 |
| 94 | 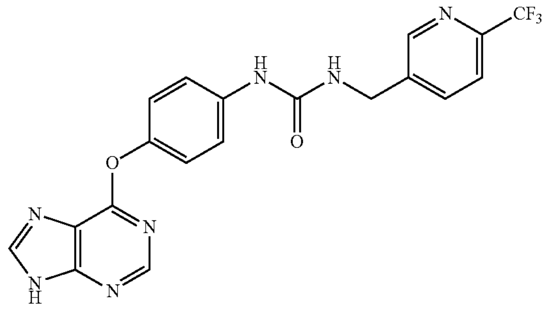 [SMILES: O=C(NCc1ccc(C(F)(F)F)nc1)Nc1ccc(Oc2ncnc3[nH]cnc23)cc1] | 429 | 430 |
| 95 | 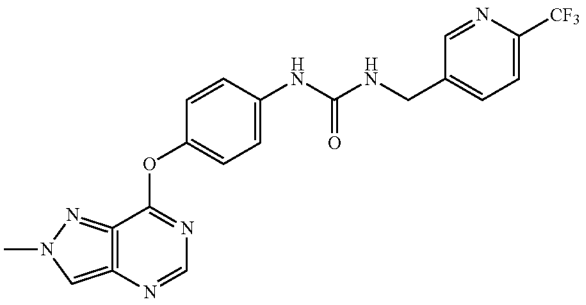 | 443 | 444 |

TABLE 1-continued
| Compound | Structure | Calculated Mass | Mass $[M + H]^+$ |
| --- | --- | --- | --- |
| Exemplary heterocyclic compounds | | | |
| 96 | 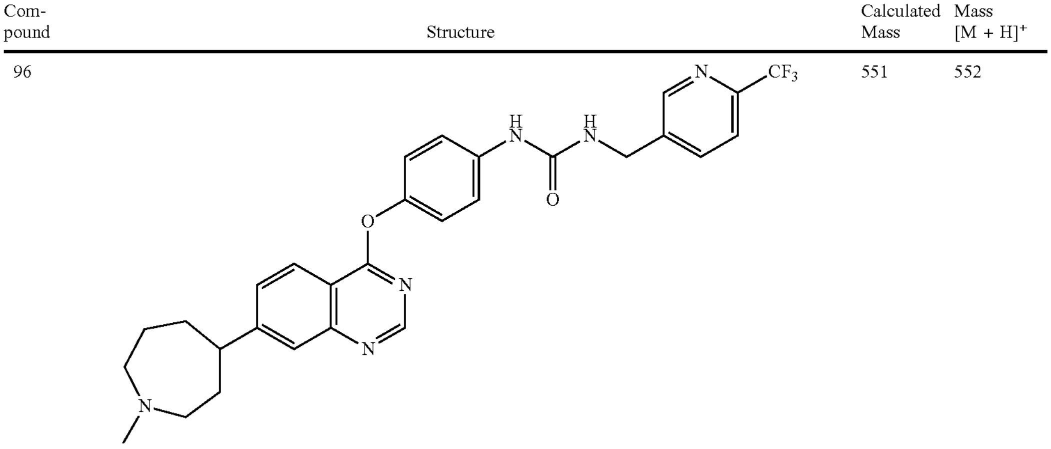 | 551 | 552 |
| 97 | 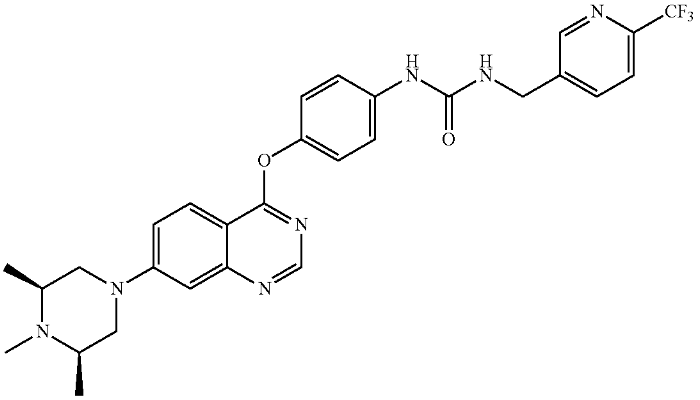 [SMILES: C[C@@H]1CN(c2ccc3c(Oc4ccc(NC(=O)NCc5ccc(C(F)(F)F)nc5)cc4)ncnc3c2)C[C@H](C)N1C] | 565 | 566 |
| 98 | 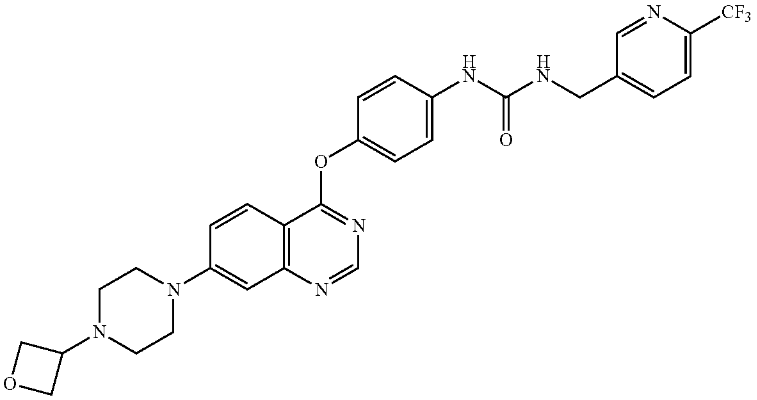 [SMILES: O=C(NCc1ccc(C(F)(F)F)nc1)Nc1ccc(Oc2ncnc3cc(N4CCN(C5COC5)CC4)ccc23)cc1] | 579 | 580 |
| 99 | 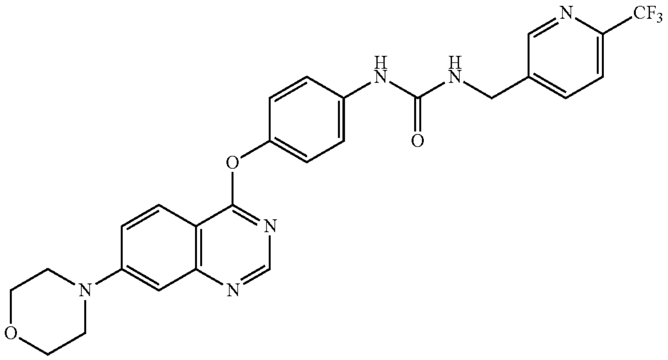 [SMILES: O=C(NCc1ccc(C(F)(F)F)nc1)Nc1ccc(Oc2ncnc3cc(N4CCOCC4)ccc23)cc1] | 524 | 525 |

TABLE 1-continued
| Exemplary heterocyclic compounds | | | |
| --- | --- | --- | --- |
| Compound | Structure | Calculated Mass | Mass [M + H]+ |
| 100 | 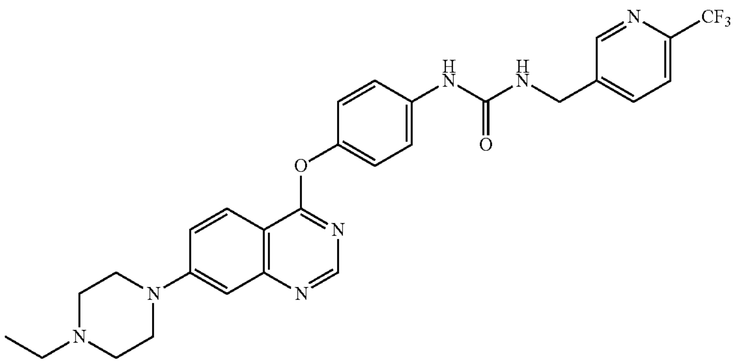 [SMILES: CCN1CCN(c2ccc3c(Oc4ccc(NC(=O)NCc5ccc(C(F)(F)F)nc5)cc4)ncnc3c2)CC1] | 551 | 552 |
| 101 | 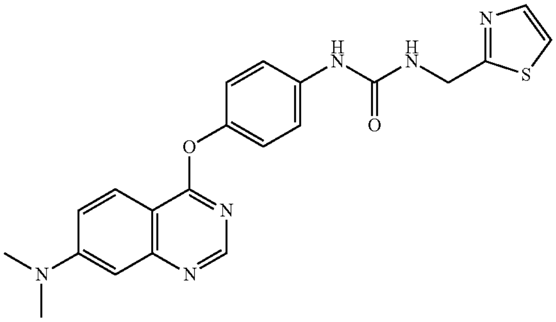 | 420 | 421 |
| 102 | 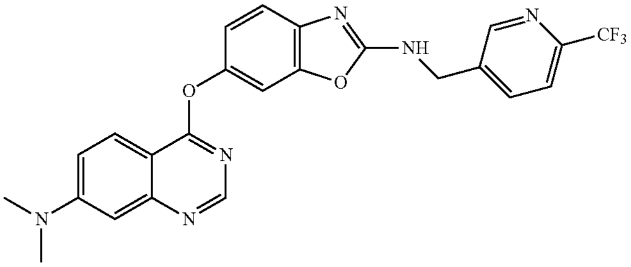 [SMILES: CN(C)c1ccc2c(Oc3ccc4nc(NCc5ccc(C(F)(F)F)nc5)oc4c3)ncnc2c1] | 480 | 481 |
| 103 | 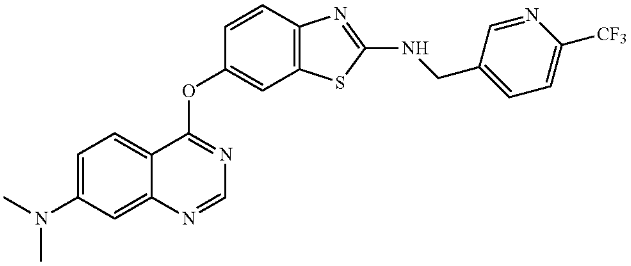 [SMILES: CN(C)c1ccc2c(Oc3ccc4nc(NCc5ccc(C(F)(F)F)nc5)sc4c3)ncnc2c1] | 496 | 497 |

TABLE 1-continued
| Exemplary heterocyclic compounds | | | |
|---|---|---|---|
| Compound | Structure | Calculated Mass | Mass [M + H]+ |
| 104 | 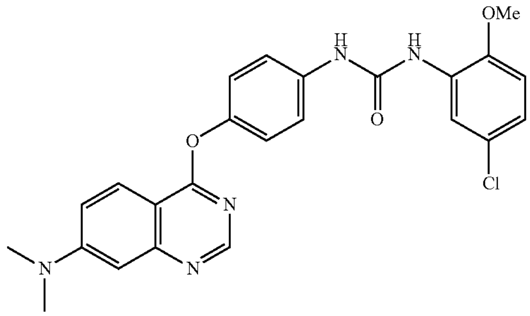 [SMILES: COc1ccc(Cl)cc1NC(=O)Nc1ccc(Oc2ncnc3cc(N(C)C)ccc23)cc1] | 463<br>465 | 464<br>466 |
| 105 | 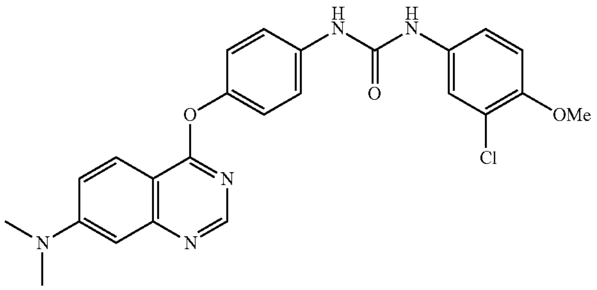 [SMILES: COc1ccc(NC(=O)Nc2ccc(Oc3ncnc4cc(N(C)C)ccc34)cc2)cc1Cl] | 463<br>465 | 464<br>466 |
| 106 | 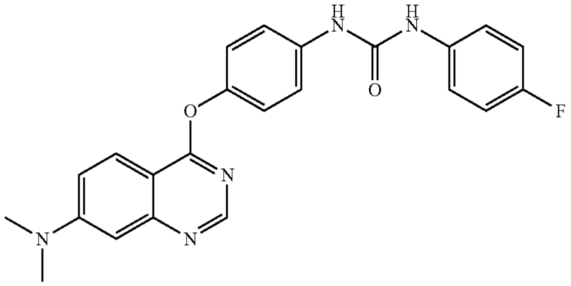 [SMILES: CN(C)c1ccc2c(Oc3ccc(NC(=O)Nc4ccc(F)cc4)cc3)ncnc2c1] | 417 | 418 |
| 107 | 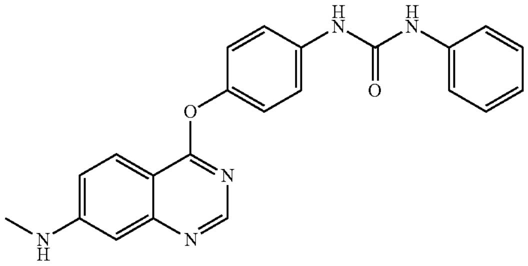 [SMILES: CNc1ccc2c(Oc3ccc(NC(=O)Nc4ccccc4)cc3)ncnc2c1] | 385 | 386 |

TABLE 1-continued

| Exemplary heterocyclic compounds | | | |
|---|---|---|---|
| Compound | Structure | Calculated Mass | Mass $[M + H]^+$ |
| 108 | 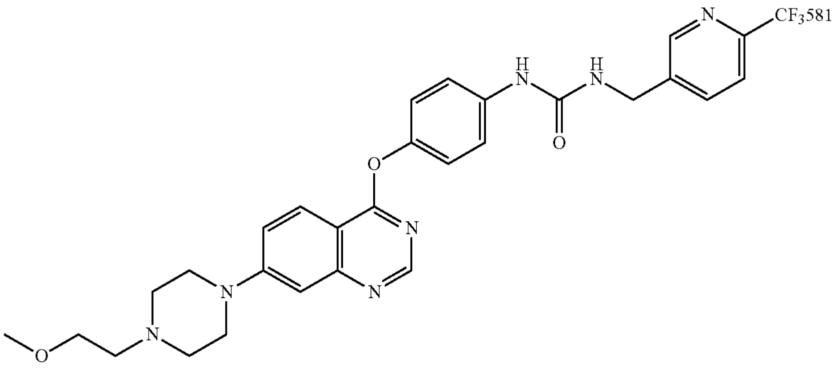 | 581 | 582 |

Example 2: CSF1R Kinase Assay

A study was conducted to test certain compounds described in EXAMPLE 1 in inhibiting CSF1R kinase activity. Results from this study are shown in Table 2 below (see column 2).

Activity of CSF1R kinase was determined using a CSF1R Kinase-Glo assay. Recombinant N-terminal GST-CSF1R (CSF1R residues L534-C972) containing the CSFIR kinase domain was expressed in Sf9 insect cells and purified. The kinase assay was carried out in 96-well plates at 30° C. for 180 min with the tested compounds in a final volume of 50 µl including the following components: 25 mM Tris-HCl pH 7.4, 4 mM $MnCl_2$, 10 mM $MgCl_2$, 0.01% BSA, 0.5 mM $NA_3VO_4$, 0.02% Triton X-100, 40 µM ATP, 2 mM DTT and 20 µM poly(Glu,Tyr) 4:1 peptide, and 600 ng recombinant GST-CSF1R. Following incubation, 50 µl Kinase-Glo Plus Reagent (Promega, Madison, WI, USA) was added and the mixture was incubated at 25° C. for 20 min. A 70-µL aliquot of each reaction mixture was transferred to a black microtiter plate and luminescence was measured on Wallac Vector 1420 multilabel counter (PerkinElmer, Shelton, CT, USA). Percentage inhibition values were obtained by comparison of reaction rate with the rates in control wells (i.e., in the absence of test compound). $IC_{50}$ values were calculated from a series of percentage inhibition values determined at a range of test compound concentrations using GraphPad Prism version 6 software (GraphPad, San Diego, CA, USA).

Example 3: Cellular Proliferation Assays

Studies were conducted to evaluate in vivo anticancer activity of certain compounds described in EXAMPLE 1 using 3-(4,5-dimethylthiazol-2-yl)-5-(3-carboxymethoxyphenyl)-2-(4-sulfophenyl)-2H-tetrazolium) (MTS) cell viability assays. Results from these studies are shown in Table 2 below (see columns 3 and 4).

Cell Line and Culture:

The cell lines M-NFS-60 (ATCC® CRL-1838™) and BaF3-CSF1R-1600 were obtained from American Type Culture Collection (ATCC, Manassas, VA, USA). The stable BaF3-CSF1R-1600 cell line expresses ETV6-CSF1R fusion protein consisting of N-terminal ETS-variant gene 6 protein (ETV6 residues M1-G337) and CSF1R tyrosine kinase (CSF1R residues L533-C972). The M-NSF-60 and BaF3-CSF1R-1600 cells were cultured in RPMI1640 medium supplemented with 10% fetal bovine serum, 0.05 mM 2-ME, 10 U/ml penicillin, and 10 g/ml streptomycin at 37° C. and 5% $CO_2$.

MTS Cell Viability Assays:

M-NFS-60 and BaF3-CSF1R-1600 cells were seeded in 96-well plates at a density of 10000 cells/100 µl and 8000 cells/100 µl per well, respectively, for 16 h and treated with vehicle or various concentrations of test compounds in medium for 72 h. Viable cells were quantified using the MTS method (Promega, Madison, WI, USA) according to manufacturer's recommended protocol. The results were determined by measuring absorbance at 490 nm using a plate reader (Victor 2). The $GI_{50}$ value was defined as the amount of compound that caused 50% reduction in cell viability in comparison with DMSO-treated (vehicle) control and was calculated using Prism GraphPad Prism version 6 software (GraphPad).

TABLE 2

Inhibitory activity of heterocyclic compounds in a CSF1R kinase assay and in M-NFS-60 and BaF3-CSF1R cell assays

| | Enzymatic Assay CSF1R | Cellular Proliferation Assay | |
|---|---|---|---|
| Compound | enzyme $IC_{50}$, (nM) | M-NFS-60 (nM) $GI_{50}$ (nM) | BaF3-CSF1R $GI_{50}$ (nM) |
| 1 | +++ | ++ | ++ |
| 2 | +++ | +++ | +++ |
| 3 | +++ | +++ | +++ |
| 4 | +++ | +++ | +++ |
| 5 | +++ | ++ | |
| 6 | +++ | | |
| 7 | + | | |
| 8 | ++ | | |
| 9 | +++ | +++ | +++ |
| 10 | +++ | ++ | ++ |
| 11 | +++ | +++ | +++ |
| 12 | +++ | | |
| 13 | ++ | | |
| 14 | ++++ | ++ | ++++ |
| 15 | ++++ | ++ | +++ |
| 16 | ++++ | +++ | +++ |
| 17 | ++++ | +++ | +++ |
| 18 | ++++ | ++ | +++ |
| 19 | ++++ | +++ | ++++ |

TABLE 2-continued

Inhibitory activity of heterocyclic compounds in a CSF1R kinase assay and in M-NFS-60 and BaF3-CSF1R cell assays

| Compound | Enzymatic Assay CSF1R enzyme $IC_{50}$, (nM) | Cellular Proliferation Assay M-NFS-60 (nM) $GI_{50}$ (nM) | BaF3-CSF1R $GI_{50}$ (nM) |
|---|---|---|---|
| 20 | ++++ | +++ | +++ |
| 21 | ++++ | +++ | +++ |
| 22 | ++ | | |
| 23 | +++ | +++ | +++ |
| 24 | ++++ | +++ | +++ |
| 25 | +++ | + | ++ |
| 26 | +++ | ++ | +++ |
| 27 | ++++ | +++ | +++ |
| 28 | +++ | +++ | ++++ |
| 29 | ++ | | |
| 30 | ++++ | +++ | +++ |
| 31 | ++ | + | ++ |
| 32 | +++ | + | ++ |
| 33 | +++ | ++ | ++ |
| 34 | ++++ | ++ | ++++ |
| 35 | + | | |
| 36 | +++ | ++ | |
| 37 | ++ | | |
| 38 | + | | |
| 39 | ++++ | ++ | |
| 40 | +++ | ++ | +++ |
| 41 | +++ | | ++ |
| 42 | ++++ | ++ | +++ |
| 43 | +++ | ++ | ++ |
| 44 | ++++ | ++ | +++ |
| 45 | ++++ | ++ | +++ |
| 47 | + | | |
| 49 | ++++ | + | ++ |
| 50 | +++ | | |
| 51 | ++++ | +++ | +++ |
| 52 | ++ | | |
| 53 | ++ | | |
| 54 | ++ | | |
| 55 | +++ | | |
| 56 | +++ | ++ | +++ |
| 57 | ++++ | ++ | ++ |
| 58 | ++++ | ++ | +++ |
| 59 | ++++ | +++ | +++ |
| 60 | +++ | | |
| 61 | ++ | | |
| 62 | ++++ | | ++ |
| 63 | +++ | ++ | ++ |
| 64 | + | | |
| 65 | ++++ | +++ | +++ |
| 66 | ++++ | +++ | +++ |
| 67 | +++ | ++ | +++ |
| 68 | +++ | ++ | +++ |
| 69 | + | | |
| 71 | ++ | | |
| 72 | + | | |
| 73 | +++ | | |
| 75 | + | | |
| 77 | ++ | | |
| 79 | ++++ | | |
| 83 | ++ | | |
| 84 | ++ | | |
| 85 | +++ | | |
| 87 | + | | |
| 89 | ++ | | |
| 90 | ++ | | |
| 93 | +++ | | |
| 97 | +++ | +++ | +++ |
| 98 | ++++ | +++ | ++++ |
| 99 | ++++ | +++ | +++ |
| 100 | ++++ | +++ | +++ |
| 101 | +++ | ++ | ++ |
| 102 | +++ | + | ++ |
| 104 | +++ | ++ | +++ |
| 105 | +++ | +++ | +++ |
| 106 | ++++ | ++ | + |
| 107 | +++ | | |
| 108 | +++ | +++ | +++ |

[a] ++++: $IC_{50} < 20$ nM; +++: 20 nM $< IC_{50} <$ 100 nM; ++: 100 nM $< IC_{50} <$ 1000 nM; +:

[b] ++++: $GI_{50} < 20$ nM; +++: 20 nM $< GI_{50} <$ 100 nM; ++: 100 nM $< GI_{50} <$ 1000 nM; +:

Example 4. Kinase Selectivity Profile

A study was conducted to determine kinase selectivity of compounds 27 and 67. More specifically, each compound was tested for inhibitory activity of CSF1R kinase, as compared to that of seven other kinases, i.e., Aurora A, Aurora B, tyrosine-protein kinase Kit (c-Kit), fms-like tyrosine kinase 3 (FLT3), platelet-derived growth factor receptor (PDGFR) A, PDGFR B, and discoidin domain receptor tyrosine kinase 1 (DDR1). Results from this study are shown in Table 3 below.

In vitro profiling of the kinase panel was performed at Reaction Biology Corporation (www.reactionbiology.com, Malvern, PA) using the "HotSpot" assay platform. Briefly, specific kinase/substrate pairs along with required cofactors were prepared in a reaction buffer containing 20 mM Hepes pH 7.5, 10 mM $MgCl_2$, 1 mM EGTA, 0.02% Brij35, 0.02 mg/ml BSA, 0.1 mM $NA_3VO_4$, 2 mM DTT, and 1% DMSO. Compound 27 or 67 was added. 20 minutes later, a mixture of ATP (Sigma, St. Louis MO) and $^{33}P$ ATP (Perkin Elmer, Waltham MA) was added to the resulting reaction solution to give a final concentration of 10 μM. The reaction was carried out at room temperature for 120 min., followed by spotting the reaction solution onto P81 ion exchange filter paper (Whatman Inc., Piscataway, NJ). Unbound phosphate was removed by extensive washing filters in 0.75% phosphoric acid. After subtracting the background derived from a control reaction containing an inactive enzyme, kinase activity was determined as the percentage of the remaining kinase activity in a test sample compared to a vehicle (DMSO) reaction. An $IC_{50}$ value and a dose-response curve for each compound against each kinase were obtained using Prism (Graph Pad Software). Selectivity, expressed as an $IC_{50}$ ratio, was determined by dividing the $IC_{50}$ value of a kinase, e.g., Aurora A, by that of CSF1R.

TABLE 3

| Kinase selectivity profile | | | | | | | | |
|---|---|---|---|---|---|---|---|---|
| | Kinase $IC_{50}$ (nM) | | | | | | | |
| Compound | CSF1R | Aurora A | Aurora B | c-Kit | FLT3 | PDGFR A | PDGFR B | DDR1 |
| 27 | 0.534 | ++++ | +++ | ++ | +++ | ++ | ++ | +++ |
| 67 | 5.69 | +++ | +++ | +++ | +++ | ++ | +++ | + |

++++: $IC_{50}$ ratio > 1000;
+++: 1000 > $IC_{50}$ ratio > 100;
++: 100 > $IC_{50}$ ratio > 10;
+: 10 > $IC_{50}$ ratio > 1

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of formula I:

I

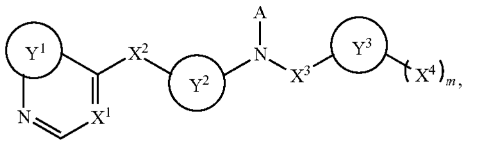

wherein

A is H or $C_1$-$C_6$ alkyl;

$Y^1$ is phenyl substituted with $(R^1)_n$, in which $R^1$ in $(R^1)_n$, n being 1-4, is, independently, F, Cl, Br, $NO_2$, CN, amino, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, 5- to 15-membered heterocycloalkyl, carbonyl, thionyl, iminyl, or spiroamino, and at least one $R^1$ is amino or 5- to 15-membered heterocycloalkyl;

$X^1$ is N;

$X^2$ is O;

$Y^2$ is

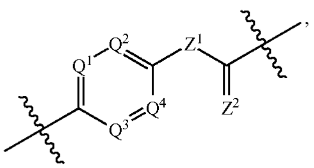

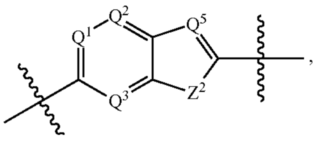

-continued

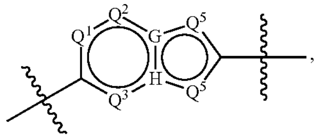

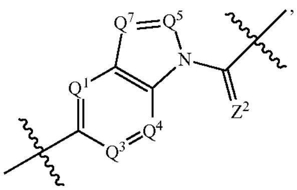

, or

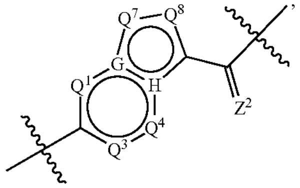

in which each of $Q^1$, $Q^2$, $Q^3$, $Q^4$, $Q^5$, $Q^6$, $Q^7$, and $Q^8$ is, independently, N or $CR^4$, $R^4$ being H, F, Cl, Br, CN, amino, $C_1$-$C_6$ alkyl, $C_1$-$C_6$ haloalkyl, or $C_1$-$C_6$ alkoxyl; $Z^1$ is O, S, or NRr, Rr being H or $C_1$-$C_6$ alkyl; $Z^2$ is O, S, or NRr; and G and H are, respectively, C or N and N or C;

$X^3$ is deleted, $CH_2$, $(CH_2)_2$, or CH(C≡CH);

$Y^3$ is $C_1$-$C_6$ alkyl, aryl, heteroaryl, $C_3$-$C_8$ cycloalkyl, or $C_5$-$C_6$ heterocycloalkyl having one heteroatom, in which the one heteroatom is O or N; and $X^4$ in $(X^4)_m$, m being 0-5, is, independently, F, Cl, Br, CN, $SO_2NH_2$, amino, $C_1$-$C_6$ alkyl, $C_1$-$C_6$ haloalkyl, or $C_1$-$C_6$ alkoxyl.

2. The compound of claim 1, wherein $Y^1$ is phenyl substituted with $R^1$ selected from amino and 5- to 15-membered heterocycloalkyl.

3. The compound of claim 2, wherein $Y^2$ is

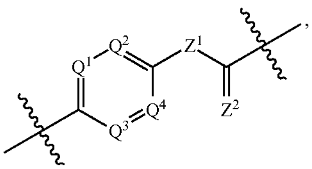

$Y^3$ is pyridyl, and $R^1$ is 5- to 15-membered heterocycloalkyl.

4. The compound of claim 1, wherein $Y^2$ is

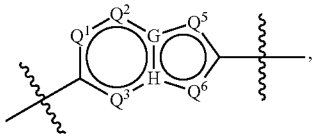

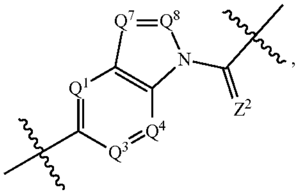

or

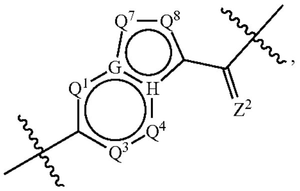

in which $Z^2$ is O or NRr.

5. The compound of claim 4, wherein $Y^2$ is

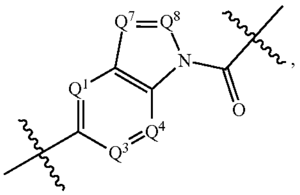

$Y^3$ is pyridyl, and $R^1$ is amino.

6. The compound of claim 1, wherein the compound is of formula Ia:

Ia

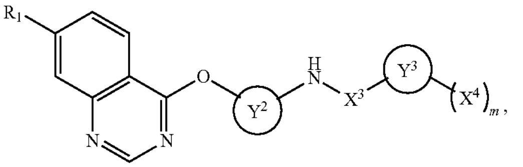

in which $R^1$ is amino or 5- to 15-membered heterocycloalkyl.

7. The compound of claim 6, wherein $Y^2$ is

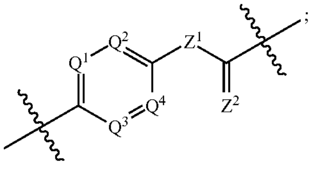

$Y^3$ is pyridyl; $X^3$ is $CH_2$; $X^4$ is $CH_3$, $CH_2F$, $CHF_2$, $CF_3$, or $OCH_3$; and m is 1.

8. The compound of claim 6, wherein $Y^2$ is

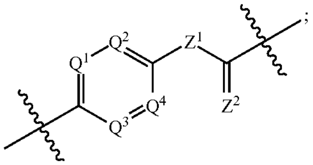

$Y^3$ is phenyl; $X^3$ is $CH_2$; each of $X^4$ is, independently, F, Cl, Br, CN, $SO_2NH_2$, $CH_3$, $CH_2F$, $CHF_2$, $CF_3$, $OCF_3$, $C_1$-$C_6$ alkoxyl, or amino; and m is 0-2.

9. The compound of claim 6, wherein $Y^2$ is

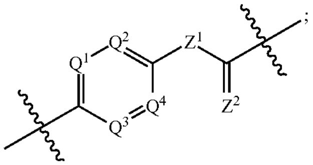

$Y^3$ is phenyl; $X^3$ is deleted; each of $X^4$ is, independently, F, Cl, Br, CN, $SO_2NH_2$, $CH_3$, $CH_2F$, $CHF_2$, $CF_3$, $OCF_3$, $C_1$-$C_6$ alkoxyl, or amino; and m is 0-2.

10. The compound of claim 7, wherein $R^1$ is amino.

11. The compound of claim 6, wherein $Y^2$ is

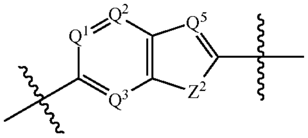

or

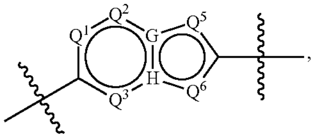

$Y^3$ is phenyl or pyridyl; and $X^3$ is $CH_2$.

12. The compound of claim 11, wherein $Y^2$ is

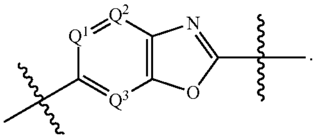

13. The compound of claim 6, wherein $Y^2$ is

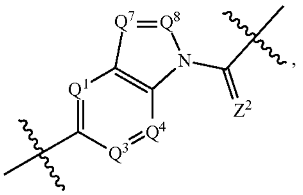

or

-continued

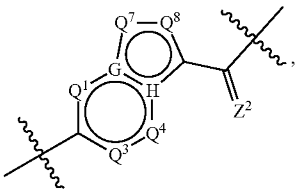

$Y^3$ is phenyl or pyridyl; and $X^3$ is $CH_2$.

14. The compound of claim 13, wherein $Y^2$ is

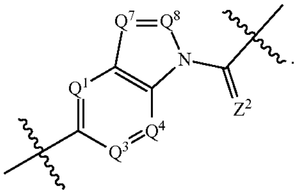

15. The compound of claim 1, wherein the compound is of formula Ib:

Ib

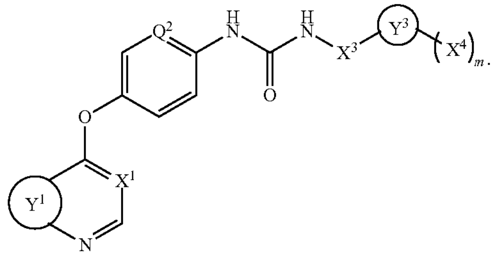

16. The compound of claim 15, wherein $Y^1$ is

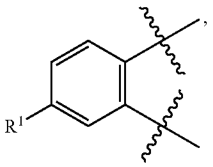

$Y^3$ is phenyl or pyridyl; and $X^3$ is deleted or $CH_2$.

17. The compound of claim 16, wherein each of $X^4$ is, independently, $CH_3$, $CH_2F$, $CHF_2$, $CF_3$, or $OCH_3$ and m is 0-2.

18. The compound of claim 1, wherein the compound is one of the following compounds:

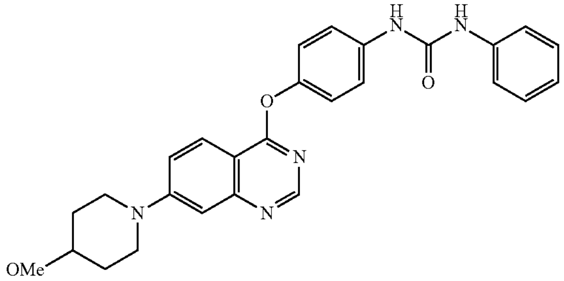

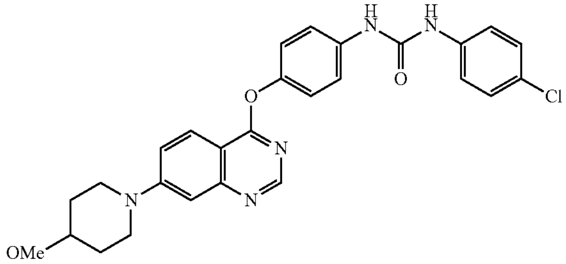

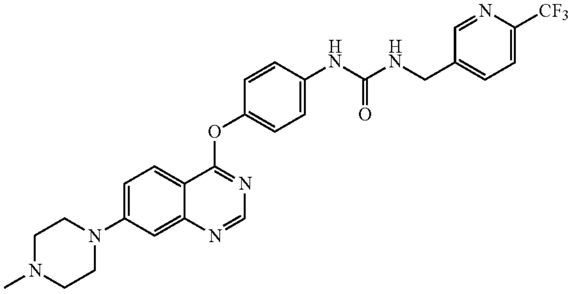

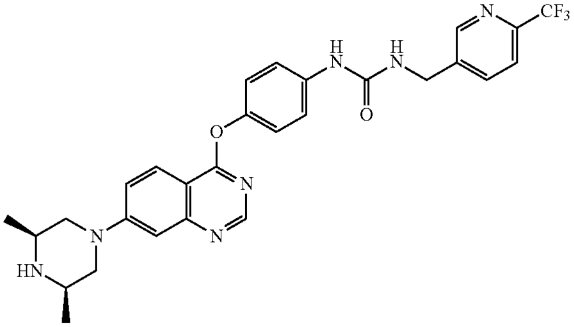

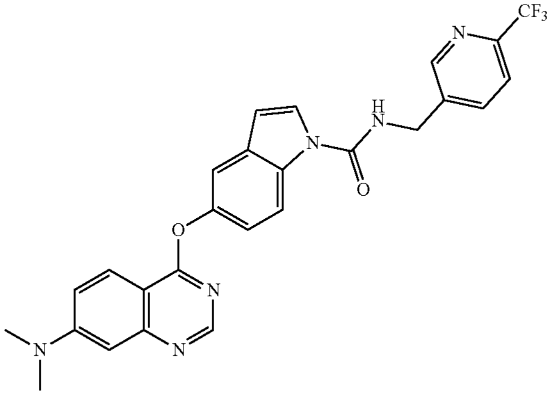

-continued
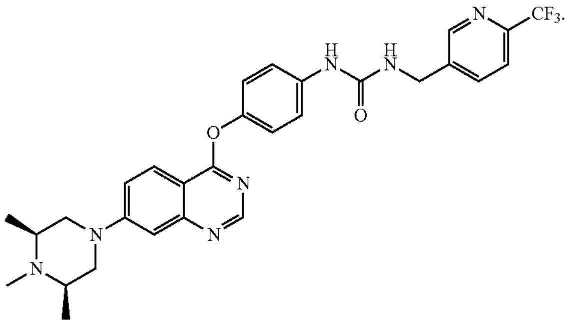
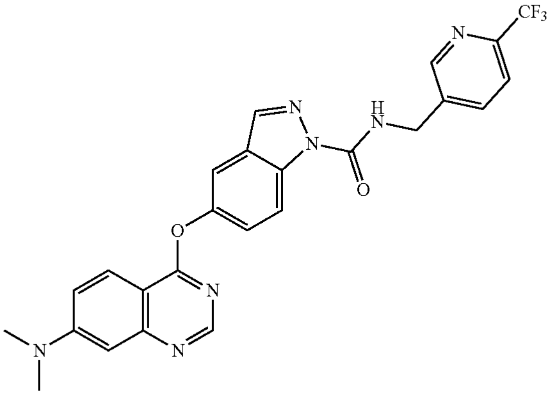
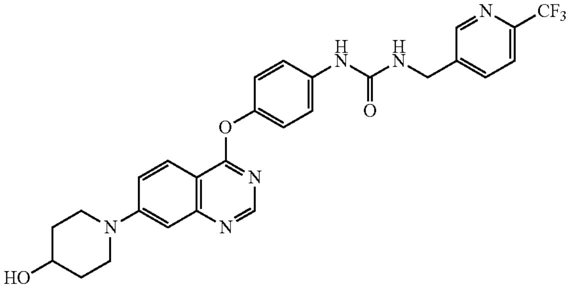
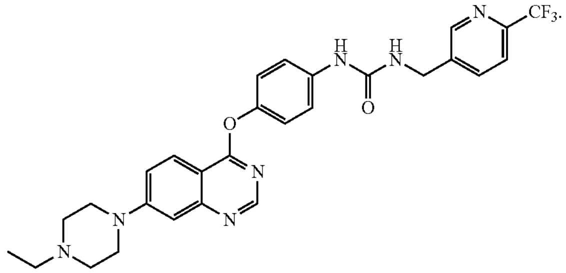
19. The compound of claim 1, wherein the compound is
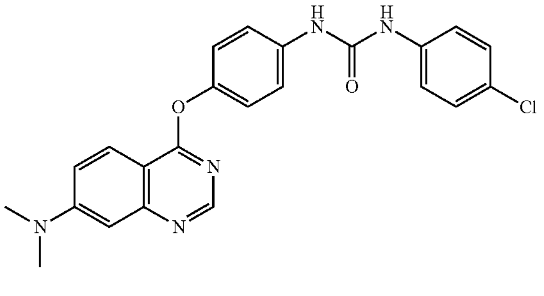
-continued
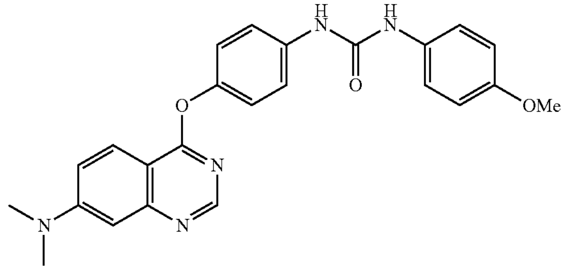
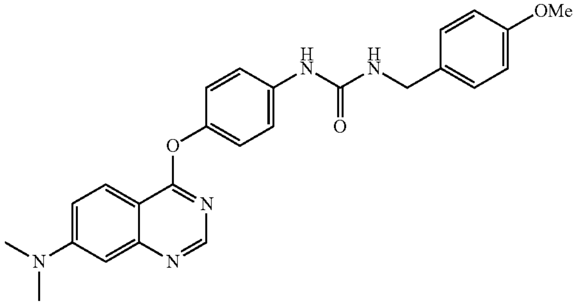
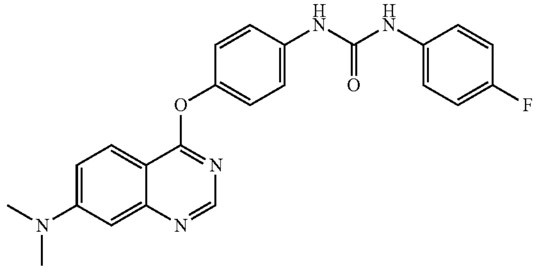
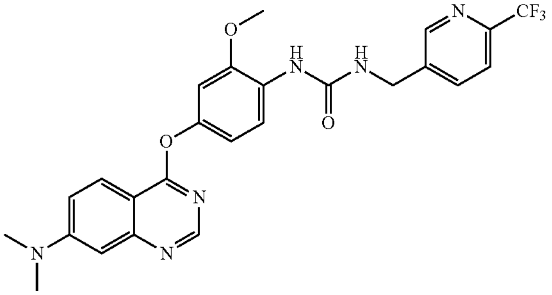
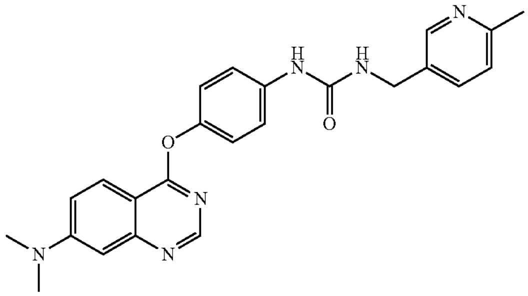
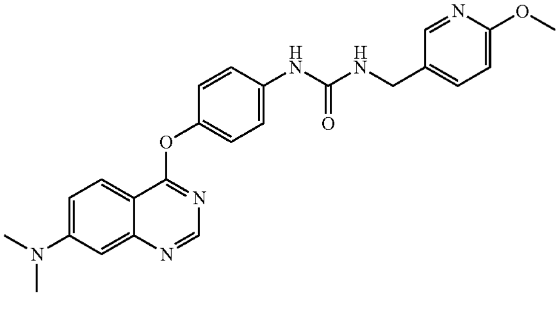

-continued
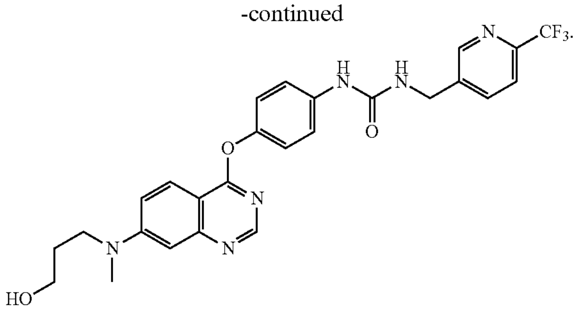
20. The compound of claim 1, wherein the compound is
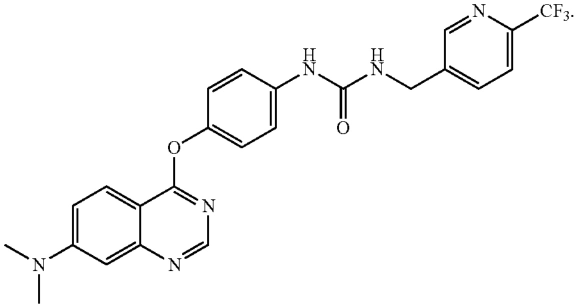 [SMILES: CN(C)c1ccc2c(Oc3ccc(NC(=O)NCc4ccc(C(F)(F)F)nc4)cc3)ncnc2c1]
* * * * *